(12) United States Patent
Keener et al.

(10) Patent No.: US 6,627,197 B2
(45) Date of Patent: Sep. 30, 2003

(54) SELECTIVE DESTRUCTION OF CELLS INFECTED WITH HUMAN IMMUNODEFICIENCY VIRUS

(75) Inventors: William K. Keener, Idaho Falls, ID (US); Thomas E. Ward, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 19 days.

(21) Appl. No.: 09/785,921

(22) Filed: Jun. 15, 2001

(65) Prior Publication Data

US 2002/0094334 A1 Jul. 18, 2002

Related U.S. Application Data

(60) Provisional application No. 60/182,759, filed on Feb. 16, 2000.

(51) Int. Cl.$^7$ .............................................. A61K 39/395
(52) U.S. Cl. ................... 424/183.1; 424/94.1; 530/327; 530/350; 530/370; 530/377; 530/826; 514/2; 435/23
(58) Field of Search ............................ 514/2; 530/350, 530/370, 327, 377, 826; 424/94.1, 183.1; 435/23

(56) References Cited

U.S. PATENT DOCUMENTS

| | | | |
|---|---|---|---|
| 5,591,829 A | 1/1997 | Matsushita | 530/391.1 |
| 5,633,388 A | 5/1997 | Diana et al. | 514/393 |
| 5,645,836 A | 7/1997 | Kitto | 424/159.1 |
| 5,677,274 A | 10/1997 | Leppla et al. | 514/2 |
| 5,684,024 A | 11/1997 | Diana et al. | 514/364 |
| 5,767,072 A | 6/1998 | Vitetta et al. | 424/194.1 |
| 5,821,243 A | 10/1998 | Diana et al. | 544/238 |
| 5,830,894 A | 11/1998 | Pevear et al. | 514/243 |
| 5,834,599 A | 11/1998 | Chang et al. | 530/388.35 |
| 5,935,957 A | 8/1999 | Diana et al. | 514/247 |
| 6,333,303 B1 * | 12/2001 | Borgford | 514/2 |

FOREIGN PATENT DOCUMENTS

WO 97/41233 * 11/1997

OTHER PUBLICATIONS

Lord, J.M., et al, "Ricin: Structure, Mode of Action, and Some Current Applications", *The FASEB Journal*, vol. 8 pp. 201 and 206, 2/94.

Richardson, P.T, et al, "Recombinant Proricin Binds Galactose But Does Not Depurinate 28 S Ribosomal RNA," *FEBS 07564*, vol. 255, No. 1, p. 15, 9/89.

Westby, M.W., et al, "Preparation and Characterization of Recombinant, Proricin Containing an Alternative Protease–Sensitive Linker Sequence," *Bioconjugate Chemistry*, 1992, 3, p. 375.

Darket, P.L., et al., "Human Immunodeficiencey Virus Protease," *Journal of Biological Chemistry*, vol. 264, No. 4, p. 2307 1989.

Jordan, S.P., et al, "Activity and Dimerization of Human Immunodeficiency Virus Protease as a Function of Solvent Composition and Enzyme Concentration," *Journal of Biological Chemistry*, vol. 267, No. 28, p. 20028. 1992.

Van Quen, M.G., "Rationale for the Use of Immunotixins in the Treatment of HIV–Infected Humans," *Journal of Drug Targeting*, vol. 5, No. 2 p. 75, 1997.

Wachinger, M., et al, "Bryodin, a Single–Chaim Ribosome–Inactivating Protein, Selectively Inhibits the Grown of HIV–1–Infected Cells and Reduces HIV–1 Production," *Research in Experimental Medicine*, 193:1–2, 1993.

Till, M.A., et al, "HIV–Infected Cells are Killed by rCF4–Ricin A Chain," *Science*, vol. 24 p. 1166.

* cited by examiner

*Primary Examiner*—Jeffrey Stucker
(74) *Attorney, Agent, or Firm*—Clayton Howarth & Cannon

(57) ABSTRACT

Compositions and methods for selectively killing a cell containing a viral protease are disclosed. The composition is a variant of a protein synthesis inactivating toxin wherein a viral protease cleavage site is interposed between the A and B chains. The variant of the type II ribosome-inactivating protein is activated by digestion of the viral protease cleavage site by the specific viral protease. The activated ribosome-inactivating protein then kills the cell by inactivating cellular ribosomes. A preferred embodiment of the invention is specific for human immunodeficiency virus (HIV) and uses ricin as the ribosome-inactivating protein. In another preferred embodiment of the invention, the variant of the ribosome-inactivating protein is modified by attachment of one or more hydrophobic agents. The hydrophobic agent facilitates entry of the variant of the ribosome-inactivating protein into cells and can lead to incorporation of the ribosome-inactivating protein into viral particles. Still another preferred embodiment of the invention includes a targeting moiety attached to the variants of the ribosome-inactivating protein to target the agent to HIV infectable cells.

43 Claims, No Drawings

SEQUENCE LISTING

<160> NUMBER OF SEQ ID NOS: 17

<210> SEQ ID NO 1
<211> LENGTH: 1698
<212> TYPE: DNA
<213> ORGANISM: Ricinus communis

<400> SEQUENCE: 1

```
atg tat gca gtg gca aca tgg ctt tgt ttt gga tcc acc tca ggg          45
Met Tyr Ala Val Ala Thr Trp Leu Cys Phe Gly Ser Thr Ser Gly
        -20                 -15                 -10 tgg tct ttc aca tta gag gat aac aac ata ttc ccc aaa caa tac          90
Trp Ser Phe Thr Leu Glu Asp Asn Asn Ile Phe Pro Lys Gln Tyr
            -5                   1                   5 cca att ata aac ttt acc aca gcg ggt gcc act gtg caa agc tac         135
Pro Ile Ile Asn Phe Thr Thr Ala Gly Ala Thr Val Gln Ser Tyr
                10                  15                  20 aca aac ttt atc aga gct gtt cgc ggt cgt tta aca act gga gct         180
Thr Asn Phe Ile Arg Ala Val Arg Gly Arg Leu Thr Thr Gly Ala
                25                  30                  35 gat gtg aga cat gat ata cca gtg ttg cca aac aga gtt ggt ttg         225
Asp Val Arg His Asp Ile Pro Val Leu Pro Asn Arg Val Gly Leu
                40                  45                  50 cct ata aac caa cgg ttt att tta gtt gaa ctc tca aat cat gca         270
Pro Ile Asn Gln Arg Phe Ile Leu Val Glu Leu Ser Asn His Ala
                55                  60                  65 gag ctt tct gtt aca tta gcc ctg gat gtc acc aat gca tat gtg         315
Glu Leu Ser Val Thr Leu Ala Leu Asp Val Thr Asn Ala Tyr Val
                70                  75                  80 gtc ggc tac cgt gct gga aat agc gca tat ttc ttt cat cct gac         360
Val Gly Tyr Arg Ala Gly Asn Ser Ala Tyr Phe Phe His Pro Asp
                85                  90                  95 aat cag gaa gat gca gaa gca atc act cat ctt ttc act gat gtt         405
Asn Gln Glu Asp Ala Glu Ala Ile Thr His Leu Phe Thr Asp Val
                100                 105                 110 caa aat cga tat aca ttc gcc ttt ggt ggt aat tat gat aga ctt         450
Gln Asn Arg Tyr Thr Phe Ala Phe Gly Gly Asn Tyr Asp Arg Leu
                115                 120                 125 gaa caa ctt gct ggt aat ctg aga gaa aat atc gag ttg gga aat         495
Glu Gln Leu Ala Gly Asn Leu Arg Glu Asn Ile Glu Leu Gly Asn
                130                 135                 140 ggt cca cta gag gag gct atc tca gcg ctt tat tat agt act         540
```

```
                                                      -continued

Gly Pro Leu Glu Glu Ala Ile Ser Ala Leu Tyr Tyr Tyr Ser Thr
        145                 150                 155 ggt ggc act cag ctt cca act ctg gct cgt tcc ttt ata att tgc        585
Gly Gly Thr Gln Leu Pro Thr Leu Ala Arg Ser Phe Ile Ile Cys
        160                 165                 170 atc caa atg att tca gaa gca gca aga ttc caa tat att gag gga        630
Ile Gln Met Ile Ser Glu Ala Ala Arg Phe Gln Tyr Ile Glu Gly
        175                 180                 185 gaa atg cgc acg aga att agg tac aac cgg aga tct gca cca gat        675
Glu Met Arg Thr Arg Ile Arg Tyr Asn Arg Arg Ser Ala Pro Asp
        190                 195                 200 cct agc gta att aca ctt gag aat agt tgg ggg aga ctt tcc act        720
Pro Ser Val Ile Thr Leu Glu Asn Ser Trp Gly Arg Leu Ser Thr
        205                 210                 215 gca att caa gag tct aac caa gga gcc ttt gct agt cca att caa        765
Ala Ile Gln Glu Ser Asn Gln Gly Ala Phe Ala Ser Pro Ile Gln
        220                 225                 230 ctg caa aga cgt aat ggt tcc aaa ttc agt gtg tac gat gtg agt        810
Leu Gln Arg Arg Asn Gly Ser Lys Phe Ser Val Tyr Asp Val Ser
        235                 240                 245 ata tta atc cct atc ata gct ctc atg gtg tat aga tgc gca cct        855
Ile Leu Ile Pro Ile Ile Ala Leu Met Val Tyr Arg Cys Ala Pro
        250                 255                 260 cca cca tcg tca cag ttt tct ttg ctt ata agg cca gtg gta cca        900
Pro Pro Ser Ser Gln Phe Ser Leu Leu Ile Arg Pro Val Val Pro
        265                 270                 275 aat ttt aat gct gat gtt tgt atg gat cct gag ccc ata gtg cgt        945
Asn Phe Asn Ala Asp Val Cys Met Asp Pro Glu Pro Ile Val Arg
        280                 285                 290 atc gta ggt cga aat ggt cta tgt gtt gat gtt agg gat gga aga        990
Ile Val Gly Arg Asn Gly Leu Cys Val Asp Val Arg Asp Gly Arg
        295                 300                 305 ttc cac aac gga aac gca ata cag ttg tgg cca tgc aag tct aat       1035
Phe His Asn Gly Asn Ala Ile Gln Leu Trp Pro Cys Lys Ser Asn
        310                 315                 320 aca gat gca aat cag ctc tgg act ttg aaa aga gac aat act att       1080
Thr Asp Ala Asn Gln Leu Trp Thr Leu Lys Arg Asp Asn Thr Ile
        325                 330                 335 cga tct aat gga aag tgt tta act act tac ggg tac agt ccg gga       1125
Arg Ser Asn Gly Lys Cys Leu Thr Thr Tyr Gly Tyr Ser Pro Gly
        340                 345                 350 gtc tat gtg atg atc tat gat tgc aat act gct gca act gat gcc       1170
Val Tyr Val Met Ile Tyr Asp Cys Asn Thr Ala Ala Thr Asp Ala
        355                 360                 365 acc cgc tgg caa ata tgg gat aat gga acc atc ata aat ccc aga       1215
Thr Arg Trp Gln Ile Trp Asp Asn Gly Thr Ile Ile Asn Pro Arg
        370                 375                 380 tct agt cta gtt tta gca gcg aca tca ggg aac agt ggt acc aca       1260
Ser Ser Leu Val Leu Ala Ala Thr Ser Gly Asn Ser Gly Thr Thr
        385                 390                 395 ctt acg gtg caa acc aac att tat gcc gtt agt caa ggt tgg ctt       1305
Leu Thr Val Gln Thr Asn Ile Tyr Ala Val Ser Gln Gly Trp Leu
        400                 405                 410 cct act aat aat aca caa cct ttt gtt aca acc att gtt ggg cta       1350
Pro Thr Asn Asn Thr Gln Pro Phe Val Thr Thr Ile Val Gly Leu
        415                 420                 425 tat ggt ctg tgc ttg caa gca aat agt gga caa gta tgg ata gag       1395
Tyr Gly Leu Cys Leu Gln Ala Asn Ser Gly Gln Val Trp Ile Glu
        430                 435                 440
```

```
gac tgt agc agt gaa aag gct gaa caa cag tgg gct ctt tat gca        1440
Asp Cys Ser Ser Glu Lys Ala Glu Gln Gln Trp Ala Leu Tyr Ala
            445                 450                 455 gat ggt tca ata cgt cct cag caa aac cga gat aat tgc ctt aca        1485
Asp Gly Ser Ile Arg Pro Gln Gln Asn Arg Asp Asn Cys Leu Thr
        460                 465                 470 agt gat tct aat ata cgg gaa aca gtt gtt aag atc ctc tct tgt        1530
Ser Asp Ser Asn Ile Arg Glu Thr Val Val Lys Ile Leu Ser Cys
    475                 480                 485 ggc cct gca tcc tct ggc caa cga tgg atg ttc aag aat gat gga        1575
Gly Pro Ala Ser Ser Gly Gln Arg Trp Met Phe Lys Asn Asp Gly
490                 495                 500 acc att tta aat ttg tat agt gga ttg gtg tta gat gtg agg cga        1620
Thr Ile Leu Asn Leu Tyr Ser Gly Leu Val Leu Asp Val Arg Arg
            505                 510                 515 tcg gat ccg agc ctt aaa caa atc att ctt tac cct ctc cat ggt        1665
Ser Asp Pro Ser Leu Lys Gln Ile Ile Leu Tyr Pro Leu His Gly
        520                 525                 530 gac cca aac caa ata tgg tta cca tta ttt tga                        1698
Asp Pro Asn Gln Ile Trp Leu Pro Leu Phe
    535                 540

<210> SEQ ID NO 2
<211> LENGTH: 1731
<212> TYPE: DNA
<213> ORGANISM: Ricinus communis

<400> SEQUENCE: 2 atg aaa ccg gga gga aat act att gta ata tgg atg tat gca gtg        45
Met Lys Pro Gly Gly Asn Thr Ile Val Ile Trp Met Tyr Ala Val
-35                 -30                 -25 gca aca tgg ctt tgt ttt gga tcc acc tca ggg tgg tct ttc aca        90
Ala Thr Trp Leu Cys Phe Gly Ser Thr Ser Gly Trp Ser Phe Thr
-20                 -15                 -10 tta gag gat aac aac ata ttc ccc aaa caa tac cca att ata aac        135
Leu Glu Asp Asn Asn Ile Phe Pro Lys Gln Tyr Pro Ile Ile Asn
-5              -1   1              5                   10 ttt acc aca gcg ggt gcc act gtg caa agc tac aca aac ttt atc        180
Phe Thr Thr Ala Gly Ala Thr Val Gln Ser Tyr Thr Asn Phe Ile
            15                  20                  25 aga gct gtt cgc ggt cgt tta aca act gga gct gat gtg aga cat        225
Arg Ala Val Arg Gly Arg Leu Thr Thr Gly Ala Asp Val Arg His
        30                  35                  40 gaa ata cca gtg ttg cca aac aga gtt ggt ttg cct ata aac caa        270
Glu Ile Pro Val Leu Pro Asn Arg Val Gly Leu Pro Ile Asn Gln
    45                  50                  55 cgg ttt att tta gtt gaa ctc tca aat cat gca gag ctt tct gtt        315
Arg Phe Ile Leu Val Glu Leu Ser Asn His Ala Glu Leu Ser Val
                60                  65                  70 aca tta gcg ctg gat gtc acc aat gca tat gtg gtc ggc tac cgt        360
Thr Leu Ala Leu Asp Val Thr Asn Ala Tyr Val Val Gly Tyr Arg
            75                  80                  85 gct gga aat agc gca tat ttc ttt cat cct gac aat cag gaa gat        405
Ala Gly Asn Ser Ala Tyr Phe Phe His Pro Asp Asn Gln Glu Asp
        90                  95                  100 gca gaa gca atc act cat ctt ttc act gat gtt caa aat cga tat        450
Ala Glu Ala Ile Thr His Leu Phe Thr Asp Val Gln Asn Arg Tyr
    105                 110                 115 aca ttc gcc ttt gga ggt aat tat gat aga ctt gaa caa ctt gct        495
Thr Phe Ala Phe Gly Gly Asn Tyr Asp Arg Leu Glu Gln Leu Ala
                120                 125                 130
```

```
ggt aat ctg aga gaa aat atc gag ttg gga aat ggt cca cta gag          540
Gly Asn Leu Arg Glu Asn Ile Glu Leu Gly Asn Gly Pro Leu Glu
            135                 140                 145 gag gct atc tca gcg ctt tat tat tac agt act ggt ggc act cag          585
Glu Ala Ile Ser Ala Leu Tyr Tyr Tyr Ser Thr Gly Gly Thr Gln
            150                 155                 160 ctt cca act ctg gct cgt tcc ttt ata att tgc atc caa atg att          630
Leu Pro Thr Leu Ala Arg Ser Phe Ile Ile Cys Ile Gln Met Ile
            165                 170                 175 tca gaa gca gca aga ttc caa tat att gag gga gaa atg cgc acg          675
Ser Glu Ala Ala Arg Phe Gln Tyr Ile Glu Gly Glu Met Arg Thr
            180                 185                 190 aga att agg tac aac cgg aga tct gca cca gat cct agc gta att          720
Arg Ile Arg Tyr Asn Arg Arg Ser Ala Pro Asp Pro Ser Val Ile
            195                 200                 205 aca ctt gag aat agt tgg ggg aga ctt tcc act gca att caa gag          765
Thr Leu Glu Asn Ser Trp Gly Arg Leu Ser Thr Ala Ile Gln Glu
            210                 215                 220 tct aac caa gga gcc ttt gct agt cca att caa ctg caa aga cgt          810
Ser Asn Gln Gly Ala Phe Ala Ser Pro Ile Gln Leu Gln Arg Arg
            225                 230                 235 aat ggt tcc aaa ttc agt gtg tac gat gtg agt ata tta atc cct          855
Asn Gly Ser Lys Phe Ser Val Tyr Asp Val Ser Ile Leu Ile Pro
            240                 245                 250 atc ata gct ctc atg gtg tat aga tgc gca cct cca cca tcg tca          900
Ile Ile Ala Leu Met Val Tyr Arg Cys Ala Pro Pro Pro Ser Ser
            255                 260                 265 cag ttt tct ttg ctt ata agg cca gtg gta cca aat ttt aat gct          945
Gln Phe Ser Leu Leu Ile Arg Pro Val Val Pro Asn Phe Asn Ala
            270                 275                 280 gat gtt tgt atg gat cct gag ccc ata gtg cgt atc gta ggt cga          990
Asp Val Cys Met Asp Pro Glu Pro Ile Val Arg Ile Val Gly Arg
            285                 290                 295 aat ggt cta tgt gtt gat gtt agg gat gga aga ttc cac aac gga         1035
Asn Gly Leu Cys Val Asp Val Arg Asp Gly Arg Phe His Asn Gly
            300                 305                 310 aac gca ata cag ttg tgg cca tgc aag tct aat aca gat gca aat         1080
Asn Ala Ile Gln Leu Trp Pro Cys Lys Ser Asn Thr Asp Ala Asn
            315                 320                 325 cag ctc tgg act ttg aaa aga gac aat act att cga tct aat gga         1125
Gln Leu Trp Thr Leu Lys Arg Asp Asn Thr Ile Arg Ser Asn Gly
            330                 335                 340 aag tgt tta act act tac ggg tac agt ccg gga gtc tat gtg atg         1170
Lys Cys Leu Thr Thr Tyr Gly Tyr Ser Pro Gly Val Tyr Val Met
            345                 350                 355 atc tat gat tgc aat act gca aca gat gcc acc cgc tgg caa         1215
Ile Tyr Asp Cys Asn Thr Ala Thr Asp Ala Thr Arg Trp Gln
            360                 365                 370 ata tgg gat aat gga acc atc ata aat ccc aga tct agt cta gtt         1260
Ile Trp Asp Asn Gly Thr Ile Ile Asn Pro Arg Ser Ser Leu Val
            375                 380                 385 tta gca gcg aca tca ggg aac agt ggt acc aca ctt aca gtg caa         1305
Leu Ala Ala Thr Ser Gly Asn Ser Gly Thr Thr Leu Thr Val Gln
            390                 395                 400 acc aac att tat gcc gtt agt caa ggt tgg ctt cct act aat aat         1350
Thr Asn Ile Tyr Ala Val Ser Gln Gly Trp Leu Pro Thr Asn Asn
            405                 410                 415 aca caa cct ttt gtg aca acc att gtt ggg cta tat ggt ctg tgc         1395
Thr Gln Pro Phe Val Thr Thr Ile Val Gly Leu Tyr Gly Leu Cys
```

```
ttg caa gca aat agt gga caa gta tgg ata gag gac tgt agc agt      1440
Leu Gln Ala Asn Ser Gly Gln Val Trp Ile Glu Asp Cys Ser Ser
                435                 440                 445 gaa aag gct gaa caa cag tgg gct ctt tat gca gat ggt tca ata      1485
Glu Lys Ala Glu Gln Gln Trp Ala Leu Tyr Ala Asp Gly Ser Ile
                450                 455                 460 cgt cct cag caa aac cga gat aat tgc ctt aca agt gat tct aat      1530
Arg Pro Gln Gln Asn Arg Asp Asn Cys Leu Thr Ser Asp Ser Asn
                465                 470                 475 ata cgg gaa aca gtt gtc aag atc ctc tct tgt ggc cct gca tcc      1575
Ile Arg Glu Thr Val Val Lys Ile Leu Ser Cys Gly Pro Ala Ser
                480                 485                 490 tct ggc caa cga tgg atg ttc aag aat gat gga acc att tta aat      1620
Ser Gly Gln Arg Trp Met Phe Lys Asn Asp Gly Thr Ile Leu Asn
                495                 500                 505 ttg tat agt ggg ttg gtg tta gat gtg agg gca tcg gat ccg agc      1665
Leu Tyr Ser Gly Leu Val Leu Asp Val Arg Ala Ser Asp Pro Ser
                510                 515                 520 ctt aaa caa atc att ctt tac cct ctc cat ggt gac cca aac caa      1710
Leu Lys Gln Ile Ile Leu Tyr Pro Leu His Gly Asp Pro Asn Gln
                525                 530                 535 ata tgg tta cca tta ttt tga                                      1731
Ile Trp Leu Pro Leu Phe
                540

<210> SEQ ID NO 3
<211> LENGTH: 1731
<212> TYPE: DNA
<213> ORGANISM: Ricinus communis

<400> SEQUENCE: 3 atg aaa ccg gga gga aat act att gta ata tgg atg tat gca gtg       45
Met Lys Pro Gly Gly Asn Thr Ile

```
                                       -continued

Ala Glu Ala Ile Thr His Leu Phe Thr Asp Val Gln Asn Arg Tyr
                105                 110                 115 aca ttc gcc ttt ggt ggt aat tat gat aga ctt gaa caa ctt gct       495
Thr Phe Ala Phe Gly Gly Asn Tyr Asp Arg Leu Glu Gln Leu Ala
            120                 125                 130 ggt aat ctg aga gaa aat atc gag ttg gga aat ggt cca cta gag       540
Gly Asn Leu Arg Glu Asn Ile Glu Leu Gly Asn Gly Pro Leu Glu
            135                 140                 145 gag gct atc tca gcg ctt tat tat tac agt act ggt ggc act cag       585
Glu Ala Ile Ser Ala Leu Tyr Tyr Tyr Ser Thr Gly Gly Thr Gln
            150                 155                 160 ctt cca act ctg gct cgt tcc ttt ata att tgc atc caa atg att       630
Leu Pro Thr Leu Ala Arg Ser Phe Ile Ile Cys Ile Gln Met Ile
            165                 170                 175 tca gaa gca gca aga ttc caa tat att gag gga gaa atg cgc acg       675
Ser Glu Ala Ala Arg Phe Gln Tyr Ile Glu Gly Glu Met Arg Thr
            180                 185                 190 aga att agg tac aac cgg aga tct gca cca gat cct agc gta att       720
Arg Ile Arg Tyr Asn Arg Arg Ser Ala Pro Asp Pro Ser Val Ile
            195                 200                 205 aca ctt gag aat agt tgg ggg aga ctt tca act gca att caa gag       765
Thr Leu Glu Asn Ser Trp Gly Arg Leu Ser Thr Ala Ile Gln Glu
            210                 215                 220 tct aac caa gga gcc ttt gct agt cca att caa ctg caa aga cgt       810
Ser Asn Gln Gly Ala Phe Ala Ser Pro Ile Gln Leu Gln Arg Arg
            225                 230                 235 aat ggt tcc aaa ttc agt gtg tac gat gtg agt ata tta atc cct       855
Asn Gly Ser Lys Phe Ser Val Tyr Asp Val Ser Ile Leu Ile Pro
            240                 245                 250 atc ata gct ctc atg gtg tat aga tgc gca cct cca cca tcg tca       900
Ile Ile Ala Leu Met Val Tyr Arg Cys Ala Pro Pro Pro Ser Ser
            255                 260                 265 cag ttt tct ttg ctt ata agg cca gtg gta cca aat ttt aat gct       945
Gln Phe Ser Leu Leu Ile Arg Pro Val Val Pro Asn Phe Asn Ala
            270                 275                 280 gat gtt tgt atg gat cct gag ccc ata gtg cgt atc gta ggt cga       990
Asp Val Cys Met Asp Pro Glu Pro Ile Val Arg Ile Val Gly Arg
            285                 290                 295 aat ggt cta tgt gtt gat gtt agg gat gga aga ttc cac aac gga      1035
Asn Gly Leu Cys Val Asp Val Arg Asp Gly Arg Phe His Asn Gly
            300                 305                 310 aac gca ata cag ttg tgg cca tgc aag tct aat aca gat gca aat      1080
Asn Ala Ile Gln Leu Trp Pro Cys Lys Ser Asn Thr Asp Ala Asn
            315                 320                 325 cag ctc tgg act ttg aaa aga gac aat act att cga tct aat gga      1125
Gln Leu Trp Thr Leu Lys Arg Asp Asn Thr Ile Arg Ser Asn Gly
            330                 335                 340 aag tgt tta act act tac ggg tac agt ccg gga gtc tat gtg atg      1170
Lys Cys Leu Thr Thr Tyr Gly Tyr Ser Pro Gly Val Tyr Val Met
            345                 350                 355 atc tat gat tgc aat act gct gca act gat gcc acc cgc tgg caa      1215
Ile Tyr Asp Cys Asn Thr Ala Ala Thr Asp Ala Thr Arg Trp Gln
            360                 365                 370 ata tgg gat aat gga acc atc ata aat ccc aga tct agt cta gtt      1260
Ile Trp Asp Asn Gly Thr Ile Ile Asn Pro Arg Ser Ser Leu Val
            375                 380                 385 tta gca gcg aca tca ggg aac agt ggt acc aca ctt aca gtg caa      1305
Leu Ala Ala Thr Ser Gly Asn Ser Gly Thr Thr Leu Thr Val Gln
            390                 395                 400
```

-continued

```
acc aac att tat gcc gtt agt caa ggt tgg ctt cct act aat aat        1350
Thr Asn Ile Tyr Ala Val Ser Gln Gly Trp Leu Pro Thr Asn Asn
                405                 410                 415 aca caa cct ttt gtg aca acc att gtt ggg cta tat ggt ctg tgc        1395
Thr Gln Pro Phe Val Thr Thr Ile Val Gly Leu Tyr Gly Leu Cys
                420                 425                 430 ttg caa gca aat agt gga caa gta tgg ata gag gac tgt agc agt        1440
Leu Gln Ala Asn Ser Gly Gln Val Trp Ile Glu Asp Cys Ser Ser
                435                 440                 445 gaa aag gct gaa caa cag tgg gct ctt tat gca gat ggt tca ata        1485
Glu Lys Ala Glu Gln Gln Trp Ala Leu Tyr Ala Asp Gly Ser Ile
                450                 455                 460 cgt cct cag caa aac cga gat aat tgc ctt aca agt gat tct aat        1530
Arg Pro Gln Gln Asn Arg Asp Asn Cys Leu Thr Ser Asp Ser Asn
                465                 470                 475 ata cgg gaa aca gtt gtc aag atc ctc tct tgt ggc cct gca tcc        1575
Ile Arg Glu Thr Val Val Lys Ile Leu Ser Cys Gly Pro Ala Ser
                480                 485                 490 tct ggc caa cga tgg atg ttc aag aat gat gga acc att tta aat        1620
Ser Gly Gln Arg Trp Met Phe Lys Asn Asp Gly Thr Ile Leu Asn
                495                 500                 505 ttg tat agt ggg ttg gtg tta gat gtg agg gca tcg gat ccg agc        1665
Leu Tyr Ser Gly Leu Val Leu Asp Val Arg Ala Ser Asp Pro Ser
                510                 515                 520 ctt aaa caa atc att ctt tac cct ctc cat ggt gac cca aac caa        1710
Leu Lys Gln Ile Ile Leu Tyr Pro Leu His Gly Asp Pro Asn Gln
                525                 530                 535 ata tgg tta cca tta ttt tga                                        1731
Ile Trp Leu Pro Leu Phe
                540

<210> SEQ ID NO 4
<211> LENGTH: 10
<212> TYPE: PRT
<213> ORGANISM: Human immunodeficiency virus

<400> SEQUENCE: 4

Val Ser Gln Asn Tyr Pro Ile Val Gln Asn
 1               5                  10

<210> SEQ ID NO 5
<211> LENGTH: 30
<212> TYPE: DNA
<213> ORGANISM: Artificial Sequence
<220> FEATURE:
<223> OTHER INFORMATION: Encodes the modified proricin linker sequence
      of SEQ ID NO:4.

<400> SEQUENCE: 5 gtt tct caa aac tac cca att gtt caa aat                              30
Val Ser Gln Asn Tyr Pro Ile Val Gln Asn
 1               5                  10

<210> SEQ ID NO 6
<211> LENGTH: 29
<212> TYPE: DNA
<213> ORGANISM: Artificial Sequence
<220> FEATURE:
<223> OTHER INFORMATION: Primer for amplifying the 5' portion of the
      preproricin gene and incorporating a SacI recognition site.

<400> SEQUENCE: 6
ctcgagctct gaaaccggga ggaaatact                                     29
```

<210> SEQ ID NO 7
<211> LENGTH: 50
<212> TYPE: DNA
<213> ORGANISM: Artificial Sequence
<220> FEATURE:
<223> OTHER INFORMATION: Primer for amplifying the 5' portion of the preproricin gene, mutating the linker sequence, and incorporating a MfeI recognition site.

<400> SEQUENCE: 7
ttgaacaatt gggtagtttt gagaaacaaa ctgtgacgat ggtggaggtg          50

<210> SEQ ID NO 8
<211> LENGTH: 41
<212> TYPE: DNA
<213> ORGANISM: Artificial Sequence
<220> FEATURE:
<223> OTHER INFORMATION: Primer for amplifying the 3' portion of the preproricin gene, mutating the linker sequence, and incorporating a MfeI recognition site.

<400> SEQUENCE: 8
ctacccaatt gttcaaaatt ttaatgctga tgtttgtatg g                   41

<210> SEQ ID NO 9
<211> LENGTH: 29
<212> TYPE: DNA
<213> ORGANISM: Artificial Sequence
<220> FEATURE:
<223> OTHER INFORMATION: Primer for amplifying the 3' portion of the preproricin gene and incorporating an XhoI recognition site.

<400> SEQUENCE: 9
ctcctcgagt ttaagccatc tattttcat                                 29

<210> SEQ ID NO 10
<211> LENGTH: 1805
<212> TYPE: DNA
<213> ORGANISM: Ricinus communis

<400> SEQUENCE: 10

```
ctcgagctct gaaaccggga ggaaatacta ttgtaatatg g atg tat                         47
                                             Met Tyr gca gtg gca aca tgg ctt tgt ttt gga tcc acc tca ggg tgg tct                   92
Ala Val Ala Thr Trp Leu Cys Phe Gly Ser Thr Ser Gly Trp Ser
        -20             -15                 -10 ttc aca tta gag gat aac aac ata ttc ccc aaa caa tac cca att                  137
Phe Thr Leu Glu Asp Asn Asn Ile Phe Pro Lys Gln Tyr Pro Ile
        -5              1               5 ata aac ttt acc aca gcg ggt gcc act gtg caa agc tac aca aac                  182
Ile Asn Phe Thr Thr Ala Gly Ala Thr Val Gln Ser Tyr Thr Asn
    10              15              20 ttt atc aga gct gtt cgc ggt cgt tta aca act gga gct gat gtg                  227
Phe Ile Arg Ala Val Arg Gly Arg Leu Thr Thr Gly Ala Asp Val
    25              30              35 aga cat gaa ata cca gtg ttg cca aac aga gtt ggt ttg cct ata                  272
Arg His Glu Ile Pro Val Leu Pro Asn Arg Val Gly Leu Pro Ile
    40              45              50 aac caa cgg ttt att tta gtt gaa ctc tca aat cat gca gag ctt                  317
Asn Gln Arg Phe Ile Leu Val Glu Leu Ser Asn His Ala Glu Leu
    55              60              65 tct gtt aca tta gcg ctg gat gtc acc aat gca tat gtg gtc ggc                  362
Ser Val Thr Leu Ala Leu Asp Val Thr Asn Ala Tyr Val Val Gly
    70              75              80
```

```
tac cgt gct gga aat agc gca tat ttc ttt cat cct gac aat cag      407
Tyr Arg Ala Gly Asn Ser Ala Tyr Phe Phe His Pro Asp Asn Gln
     85                  90                  95 gaa gat gca gaa gca atc act cat ctt ttc act gat gtt caa aat      452
Glu Asp Ala Glu Ala Ile Thr His Leu Phe Thr Asp Val Gln Asn
100                 105                 110 cga tat aca ttc gcc ttt ggt ggt aat tat gat aga ctt gaa caa      497
Arg Tyr Thr Phe Ala Phe Gly Gly Asn Tyr Asp Arg Leu Glu Gln
    115                 120                 125 ctt gct ggt aat ctg aga gaa aat atc gag ttg gga aat ggt cca      542
Leu Ala Gly Asn Leu Arg Glu Asn Ile Glu Leu Gly Asn Gly Pro
130                 135                 140 cta gag gag gct atc tca gcg ctt tat tat tac agt act ggt ggc      587
Leu Glu Glu Ala Ile Ser Ala Leu Tyr Tyr Tyr Ser Thr Gly Gly
145                 150                 155 act cag ctt cca act ctg gct cgt tcc ttt ata att tgc atc caa      632
Thr Gln Leu Pro Thr Leu Ala Arg Ser Phe Ile Ile Cys Ile Gln
160                 165                 170 atg att tca gaa gca gca aga ttc caa tat att gag gga gaa atg      677
Met Ile Ser Glu Ala Ala Arg Phe Gln Tyr Ile Glu Gly Glu Met
175                 180                 185 cgc acg aga att agg tac aac cgg aga tct gca cca gat cct agc      722
Arg Thr Arg Ile Arg Tyr Asn Arg Arg Ser Ala Pro Asp Pro Ser
    190                 195                 200 gta att aca ctt gag aat agt tgg ggg aga ctt tca act gca att      767
Val Ile Thr Leu Glu Asn Ser Trp Gly Arg Leu Ser Thr Ala Ile
205                 210                 215 caa gag tct aac caa gga gcc ttt gct agt cca att caa ctg caa      812
Gln Glu Ser Asn Gln Gly Ala Phe Ala Ser Pro Ile Gln Leu Gln
220                 225                 230 aga cgt aat ggt tcc aaa ttc agt gtg tac gat gtg agt ata tta      857
Arg Arg Asn Gly Ser Lys Phe Ser Val Tyr Asp Val Ser Ile Leu
    235                 240                 245 atc cct atc ata gct ctc atg gtg tat aga tgc gca cct cca cca      902
Ile Pro Ile Ile Ala Leu Met Val Tyr Arg Cys Ala Pro Pro Pro
250                 255                 260 tcg tca cag ttt gtt tct caa aac tac cca att gtt caa aat ttt      947
Ser Ser Gln Phe Val Ser Gln Asn Tyr Pro Ile Val Gln Asn Phe
265                 270                 275 aat gct gat gtt tgt atg gat cct gag ccc ata gtg cgt atc gta      992
Asn Ala Asp Val Cys Met Asp Pro Glu Pro Ile Val Arg Ile Val
280                 285                 290 ggt cga aat ggt cta tgt gtt gat gtt agg gat gga aga ttc cac     1037
Gly Arg Asn Gly Leu Cys Val Asp Val Arg Asp Gly Arg Phe His
    295                 300                 305 aac gga aac gca ata cag ttg tgg cca tgc aag tct aat aca gat     1082
Asn Gly Asn Ala Ile Gln Leu Trp Pro Cys Lys Ser Asn Thr Asp
310                 315                 320 gca aat cag ctc tgg act ttg aaa aga gac aat act att cga tct     1127
Ala Asn Gln Leu Trp Thr Leu Lys Arg Asp Asn Thr Ile Arg Ser
325                 330                 335 aat gga aag tgt tta act act tac ggg tac agt ccg gga gtc tat     1172
Asn Gly Lys Cys Leu Thr Thr Tyr Gly Tyr Ser Pro Gly Val Tyr
340                 345                 350 gtg atg atc tat gat tgc aat act gct gca act gat gcc acc cgc     1217
Val Met Ile Tyr Asp Cys Asn Thr Ala Ala Thr Asp Ala Thr Arg
    355                 360                 365 tgg caa ata tgg gat aat gga acc atc ata aat ccc aga tct agt     1262
Trp Gln Ile Trp Asp Asn Gly Thr Ile Ile Asn Pro Arg Ser Ser
```

```
                                    370                 375                 380
cta gtt tta gca gcg aca tca ggg aac agt ggt acc aca ctt aca           1307
Leu Val Leu Ala Ala Thr Ser Gly Asn Ser Gly Thr Thr Leu Thr
        385                 390                 395 gtg caa acc aac att tat gcc gtt agt caa ggt tgg ctt cct act           1352
Val Gln Thr Asn Ile Tyr Ala Val Ser Gln Gly Trp Leu Pro Thr
    400                 405                 410 aat aat aca caa cct ttt gtg aca acc att gtt ggg cta tat ggt           1397
Asn Asn Thr Gln Pro Phe Val Thr Thr Ile Val Gly Leu Tyr Gly
415                 420                 425 ctg tgc ttg caa gca aat agt gga caa gta tgg ata gag gac tgt           1442
Leu Cys Leu Gln Ala Asn Ser Gly Gln Val Trp Ile Glu Asp Cys
        430                 435                 440 agc agt gaa aag gct gaa caa cag tgg gct ctt tat gca gat ggt           1487
Ser Ser Glu Lys Ala Glu Gln Gln Trp Ala Leu Tyr Ala Asp Gly
    445                 450                 455 tca ata cgt cct cag caa aac cga gat aat tgc ctt aca agt gat           1532
Ser Ile Arg Pro Gln Gln Asn Arg Asp Asn Cys Leu Thr Ser Asp
460                 465                 470 tct aat ata cgg gaa aca gtt gtc aag atc ctc tct tgt ggc cct           1577
Ser Asn Ile Arg Glu Thr Val Val Lys Ile Leu Ser Cys Gly Pro
        475                 480                 485 gca tcc tct ggc caa cga tgg atg ttc aag aat gat gga acc att           1622
Ala Ser Ser Gly Gln Arg Trp Met Phe Lys Asn Asp Gly Thr Ile
    490                 495                 500 tta aat ttg tat agt ggg ttg gtg tta gat gtg agg gca tcg gat           1667
Leu Asn Leu Tyr Ser Gly Leu Val Leu Asp Val Arg Ala Ser Asp
505                 510                 515 ccg agc ctt aaa caa atc att ctt tac cct ctc cat ggt gac cca           1712
Pro Ser Leu Lys Gln Ile Ile Leu Tyr Pro Leu His Gly Asp Pro
        520                 525                 530 aac caa ata tgg tta cca tta ttt tgatagacag attactctct                 1756
Asn Gln Ile Trp Leu Pro Leu Phe
    535                 540 tgcagtgtgt atgtcctgcc atgaaaatag atggcttaaa ctcgaggag                 1805

<210> SEQ ID NO 11
<211> LENGTH: 10
<212> TYPE: PRT
<213> ORGANISM: Human immunodeficiency virus

<400> SEQUENCE: 11

Ser Ala Thr Ile Met Met Gln Arg Gly Asn
1               5                  10

<210> SEQ ID NO 12
<211> LENGTH: 12
<212> TYPE: PRT
<213> ORGANISM: Human immunodeficiency virus

<400> SEQUENCE: 12

Val Ser Gln Asn Tyr Pro Ile Val Gln Asn Phe Asn
1               5                  10

<210> SEQ ID NO 13
<211> LENGTH: 12
<212> TYPE: PRT
<213> ORGANISM: Human immunodeficiency virus

<400> SEQUENCE: 13

Ser Ala Thr Ile Met Met Gln Arg Gly Asn Phe Asn
```

-continued

```
<210> SEQ ID NO 14
<211> LENGTH: 12
<212> TYPE: PRT
<213> ORGANISM: Ricinus communis

<400> SEQUENCE: 14

Val Ser Ile Leu Ile Pro Ile Ile Ala Leu Met Val
 1               5                  10

<210> SEQ ID NO 15
<211> LENGTH: 5
<212> TYPE: PRT
<213> ORGANISM: Rous sarcoma virus

<400> SEQUENCE: 15

Pro Pro Pro Pro Thr
 1               5

<210> SEQ ID NO 16
<211> LENGTH: 4
<212> TYPE: PRT
<213> ORGANISM: Homo sapiens

<400> SEQUENCE: 16

Lys Asp Glu Leu
 1

<210> SEQ ID NO 17
<211> LENGTH: 5
<212> TYPE: PRT
<213> ORGANISM: Human immunodeficiency virus

<400> SEQUENCE: 17

Gly Ala Arg Ala Ser
 1               5
```

SELECTIVE DESTRUCTION OF CELLS INFECTED WITH HUMAN IMMUNODEFICIENCY VIRUS

RELATED APPLICATION

This application claims priority from U.S. provisional application Ser. No. 60/182,759 filed Feb. 16, 2000 and is incorporated by reference.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

This invention relates to antiviral agents and methods of use thereof. More particularly, the invention relates to antiviral agents that specifically destroy cells infected by viruses that produce a protease in such infected cells. The antiviral agents are activated by the viral protease, thereby specifically targeting the infected cells for destruction. Toxins that target cell surface receptors or antigens on tumor cells have attracted considerable attention for treatment of cancer. E.g., I. Pastan & D. FitzGerald, Recombinant Toxins for Cancer Treatment, 254 Science 1173–1177 (1991); Anderson et al., U.S. Pat. Nos. 5,169,933 and 5,135,736; Thorpe et al., U.S. Pat. No. 5,165,923; Jansen et al., U.S. Pat. No. 4,906,469; Frankel, U.S. Pat. No. 4,962,188; Uhr et al., U.S. Pat. No. 4,792,447; Masuho et al., U.S. Pat. Nos. 4,450,154 and 4,350,626. These agents include a cell-targeting moiety, such as an antigen-binding protein or a growth factor, linked to a plant or bacterial toxin. They kill cells by mechanisms different from conventional chemotherapy, thus potentially reducing or eliminating cross resistance to conventional chemotherapeutic agents.

Ricin and other similar plant toxins, such as abrin, modeccin and viscumin, comprise two polypeptide chains (known as the A and B chains) linked by a disulfide bridge, one chain (the A chain) being primarily responsible for the cytotoxicity and the other chain (the B chain) having sites that enable the molecule to bind to cell surfaces. Such toxins are known as type II ribosome-inactivating proteins or RIPs. F. Stirpe et al., Ribosome-inactivating Proteins from Plants: Present Status and Future Prospects, 10 Biotechnology 405–412 (1992).

Ricin is produced in the plant *Ricinus communis* (commonly known as the castor bean plant) via a precursor protein known as "preproricin." Preproricin comprises a single polypeptide chain that includes a leader sequence, the A chain, a linker peptide, and the B chain. The leader sequence is subsequently removed in the organism to yield proricin, which is then cleaved to eliminate the linker region such that the A and B chains remain connected only by a disulfide bond in the mature protein. The toxicity of ricin-type toxins operates in three phases: (1) binding to the cell surface via the B chain; (2) penetration of at least the A chain into the cytosol via intracellular organelles, and (3) inhibition of protein synthesis through the A chain cleaving an essential adenine residue from ribosomal RNA. Thus, outside the cell separated A and B chains are essentially nontoxic, because the inherently toxic A chain lacks the ability to bind to cell surfaces and enter the cells in the absence of the B chain. Moreover, preproricin and proricin are also non-toxic, since the activity of the A chain is inhibited in these precursors. It is also known that in ricintype toxins the B chain binds to cell surfaces by virtue of galactose recognition sites, which react with glycoproteins or glycolipids exposed on the cell surface. It has been suggested that the toxicity of the ricin A chain might be exploited in antitumor therapy by replacing the indiscriminately binding B chain with a different targeting component having the ability to bind only to tumor cells. Thus, various immunotoxins have been prepared consisting of a conjugate of whole ricin or a separated ricin A chain and a tumorspecific monoclonal antibody or other targeting component while previously described immunotoxins comprising ricin are generally suitable for their specific purposes, they possess certain inherent limitations that detract from their overall utility in treating viral infections. One problem with the known conjugates arises from a structural feature of the A chain from natural ricin. It is known that the natural ricin A chain becomes Nglycosylated during its synthesis, by enzymes present in Ricinus cells, and it is thought that the resulting sugar moieties are capable of nonspecific interactions with cell surfaces. Thus, it appears that the known A chain conjugates are capable of a certain amount of binding with non target cells, even in the absence of the natural B chain, thus increasing the toxicity of such immunotoxins toward non-target cells. To partially mitigate this problem, recombinant A chain that lacks carbohydrate residues has been produced in *E. coli*. S. H. Pincus & V. V. Tolstikov, Anti-Human Immunodeficiency Virus Immunoconjugates, 32 Adv. Pharmacol. 205–247 (1995). Another problem with many ricin immunoconjugates arises from the fact that the B chain seems to have an important secondary function in that it somehow assists in the intoxication process, apart from its primary function in binding the ricin molecule to the cell surfaces. This secondary function is lost if the B chain is replaced by a different targeting component, such as a monoclonal antibody. Some researchers have addressed this problem by covalent attachment of affinity reagents to the B chain such that the galactose binding sites are blocked. J. M. Lambert et al., An Immunotoxin Prepared with Blocked Ricin: a Natural Plant Toxin Adapted for Therapeutic Use, 51 Cancer Res. 6236–6242 (1991).

The aforementioned modifications of ricin seek to enhance binding specificity to the outer cell surface by immunotoxins and similar, targeted therapeutic agents. Since certain types of infected cells do not express infection-related surface antigens, such binding specificity represents an inherent limitation. S. H. Pincus & V. V. Tolstikov, supra. A targeting-independent agent with a well-defined toxin activation mechanism involving a viral protease would permit the use of nonspecific "targeting" (i.e., cell-binding) molecules, including sugar moieties and fully active ricin B chain. Therapeutic agents designed in this manner could eliminate a broader spectrum of infected cells, with potentially fewer undesirable side effects. Anti-HIV immunotoxins have been described that include antibodies linked to various toxic moieties via a peptide linker that includes a sequence cleavable by HIV protease. S. H. Pincus & V. V. Tolstikov, supra. In some cases, release of the toxic moiety by this protease may render it active, although the specific activation mechanism was not further defined. In the present invention, antibodies or segments thereof are only one of many potential targeting molecules for the therapeutic agents. Moreover, the activation mechanisms are clearly specified in the present invention. One such mechanism relies on protease-dependent cleavage at or near the natural protease activation site for a given toxin, not merely on release from a bulky "carrier" protein (i.e., antibody). S. H. Pincus & V. V. Tolstikov, supra. In the case of ricin, the natural site for cleavage by proteolytic activity in Ricinus is in a disulfide-circumscribed loop in which one cysteine resides on the A chain and the other resides on the B chain; cleavage yields A and B chains connected by a disulfide bond. Therefore, most embodiments of the present invention that involve ricin include an HIV-protease cleavage sequence fused in-frame to the C-terminus of A chain such that the natural cleavage site is replaced with the HIV-protease site in the disulfide-circumscribed loop. In these embodiments, at lease some minimal N-terminal sequence of B chain required to inhibit A chain activity is retained, such that activation requires proteolytic cleavage and reduction of the disulfide bond. In all remaining embodiments, the mechanism of activation involves cleavage of a peptide linker to A chain, thereby separating adenine-like moieties that are chemically attached to the linker. Separation of the adenine-like residues unblocks the active site of ricin and allows A chain activity. Further, the foregoing text describes preferred embodiments (i.e., full B chain functionality, sugar moieties) that are highly compatible with these activation mechanisms. Indeed, these preferred embodiments are not suggested by others. S. H. Pincus & V. V. Tolstikov, supra. Certain embodiments of the present invention comprise attachment of hydrophobic moieties for intracellular targeting to sites of viral protease activity, which is limited in the cytosol. The aforementioned immunotoxins do not possess this aspect of the invention. While attachment of hydrophobic fatty acids to ricin A chain has been presented in terms of enhancing translocation across cell membranes for hypothetical medical applications, a method for activating ricin was not presented. A. V. Kabanov et al., Fatty Acylation of Proteins for Translocation Across Cell Membrane, 1 Biomed. Sci. 33–36 (1990); V. Y. Alakhov et al., Increasing Cytostatic Effects of Ricin A Chain and *Staphylococcus aureus* Enterotoxin A Through In Vitro Hydrophobization with Fatty Acid Residues, 12 Biotechnol. Appl. Biochem. 94–98 (1990). Hydrophobization of ricin is likely to increase toxicity to non-target cells, even if cell-surface targeting moieties are attached. A separate, viral-protease-dependent mechanism for activating ricin (and similar toxins) would prevent nonspecific toxicity. The present invention combines such a mechanism with hydrophobization.

In view of the foregoing, it will be appreciated that providing an antiviral agent that is activated only in cells infected with a selected virus, is non-toxic in uninfected cells, and is targeted independently of infection-related antigens, would be a significant advancement in the art. Furthermore, the prior art teaches away from making the present invention because specific embodiments described herein have previously been described as deleterious (B chain activity). Moreover, the prior art fails to describe or suggest elements of the present invention (e.g., means for fatty acid attachment) in combination with a protease-dependent toxin activation mechanism.

BRIEF SUMMARY OF THE INVENTION

It is an object of the present invention to provide an antiviral agent that is toxic to virus-infected cells, but non-toxic to uninfected cells.

It is also an object of the invention to provide an antiviral agent for treating viral infections wherein the virus encodes a protease that is essential to virus replication.

It is another object of the invention to provide a toxin (e.g., ricin) based antiviral agent that maintains the inhibitory functionality of the lectin B chain, whereby the lectin B chain (or a portion thereof) inhibits the activity of the ricin A chain prior to proteolytic cleavage of a linker sequence and reduction of the disulfide bond. It is another object of the invention to provide a ricin- (or similar toxin) based antiviral agent that maintains the galactose-binding functionality of the ricin B chain, which enhances the binding of the antiviral agent to galactose residues on cell surfaces and the cellular internalization of the antiviral agent.

It is still another object of the invention to provide an antiviral agent for treating retroviral infections, including HIV infections.

It is yet another object of the invention to provide a method for treating retroviral infections wherein the virus encodes a protease that is essential to virus replication.

It is also an object of the invention to provide a method for treating HIV infections.

These and other objects can be addressed by providing a composition comprising a compound represented by the formula $(T_m\text{-}A\text{-}X\text{-}B)\text{-}H_n$ or $(A\text{-}X\text{-}B\text{-}T_m)H_n$, wherein A is a protein synthesis inactivating toxin that is inactive until X is digested; X is a peptide susceptible to digestion by a viral protease; B is a lectin, T is a targeting moiety, H is a hydrophobic agent, m is 0 or an integer of at least 1, and n is 0 or an integer of at least 1. In a preferred embodiment of the invention, A is a ricin A chain and B is a ricin B chain or segment thereof. In another preferred embodiment of the invention, X is susceptible to digestion by a retroviral protease, such as a human immunodeficiency virus protease. In an especially preferred embodiment, X is a member selected from the group consisting of SEQ ID NO:12 and SEQ ID NO: 13. Preferably, the targeting moiety is a member selected from the group consisting of antigen-binding proteins, viral surface components and segments thereof, growth factors, lectins, and carbohydrates. Especially preferred targeting moieties include a member selected from the group consisting of antigen-binding proteins, viral surface components and segments thereof, proteins that bind viral surface components, growth factors, lectins, and carbohydrates. For example, such targeting moieties can include a member selected from the group consisting of antibodies against HIV glycoprotein gp120, antibodies against gp41, and the CD4 protein or segments thereof. As a further example, the targeting moiety can be an antigen-binding protein that binds the CD4 glycoprotein, such as gp120 or a segment thereof. Still another illustrative targeting moiety is a GAG protein segment.

The hydrophobic agent is preferably a member selected from the group consisting of bile acids, sterols, and saturated and unsaturated fatty acids. Preferred bile acids include cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof. Preferred sterols include cholestanol, coprostanol, cholesterol, epicholesterol, ergosterol, ergocalciferol, and mixtures thereof. Preferred saturated or unsaturated fatty acid comprise about 4 to 20 carbon atoms, such as butyric acid, valeric acid, caproic acid, caprylic acid, capric acid, lauric acid, myristic acid, palmitic acid, stearic acid, oleic acid, linoleic acid, linolenic acid, eleostearic acid, and mixtures thereof.

Another preferred embodiment of the invention further comprises a pharmaceutically acceptable carrier admixed with the compound.

Still another preferred embodiment of the invention comprises a composition comprising a compound represented by the formula N-X-A or A-X-N, wherein A is a protein synthesis inactivating toxin that is inactive until digestion of X, X is a peptide susceptible to digestion by a viral protease, and N is an adenine moiety or a functional equivalent thereof. Yet another preferred embodiment of the invention comprises a method for treating a human immunodeficiency virus infection comprising administering an effective amount of a composition comprising:

(a) a member selected from the group consisting of:
  (i) a compound represented by the formula $(T_m\text{-AXB})H_n$ or $(AXBT_m)H_n$, wherein A is a protein synthesis inactivating toxin that is inactive until X is digested; X is a peptide susceptible to digestion by a human immunodeficiency virus protease; B is a lectin, T is a targeting moiety, H is a hydrophobic agent, m is 0 or an integer of at least 1, and n is 0 or an integer of at least 1,
  (ii) a compound represented by the formula N-X-A or A-X-N, wherein A is a protein synthesis inactivating toxin that is inactive until digestion of X, X is a peptide susceptible to digestion by a human immunodeficiency virus protease, and N is an adenine moiety or functional equivalent thereof, and
  (iii) mixtures of (i) and (ii); and
(b) a pharmaceutically acceptable carrier.

A further preferred embodiment of the invention comprises a nucleic acid encoding a peptide represented by the formula A-X-B wherein A is a protein synthesis inactivating toxin that is inactive until digestion of X; X is a peptide susceptible to digestion by a viral protease; and B is a lectin or other targeting moiety.

DETAILED DESCRIPTION OF THE INVENTION

Before the present antiviral agents and methods of use thereof for treating viral infections are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition comprising "a carrier" includes reference to two or more of such carriers, reference to "a fatty acid" includes reference to one or more of such fatty acids, and reference to "a targeting moiety" includes reference to two or more of such targeting moieties.

In describing and claiming the present invention, the following terminology will be used in accordance with the definitions set out below as used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "protein synthesis inactivating toxin" includes toxins that are ribonucleases, N-glycosidases, or ADP-ribosyltransferases. N-glycosidases are exemplified by the single polypeptide of the plant type I ribosome inactivating proteins (e.g., gelonin, momordin, and saporin), and the "A" chain of the plant type II ribosome-inactivating proteins (e.g., ricin, abrin, modeccin, and the like) and similar acting bacterial toxins. "Protein synthesis inactivating toxin" also includes the specific ribonucleases that digest a specific phosphodiester bond in the backbone of ribosomal RNA, thereby inactivating the ribosomes and inhibiting protein synthesis. Ribonucleases are exemplified by the fungal toxins alpha-sarcin, mitogillin, and restrictocin, but also include similar acting bacterial toxins. "Protein synthesis inactivating toxin" also includes the ADP-ribosylating component of the ADP-ribosyltransferases, which are proteolytically activated bacterial toxins that ADP-ribosylate, and thus inactivate, components of the protein synthesis machinery (e.g., diphtheria toxin, Pseudomonas exotoxin A). Plant ribosome-inactivating proteins (RIPs) are N-glycosidases that cleave the N-glycosidic bond of adenine in a specific ribosomal RNA sequence. Many RIPs are single-chain proteins (type I RIPs), but some (type II RIPs) possess a galactose-specific lectin domain that binds to cell surfaces. J. M. Ford, M. R. Hartley, L. M. Roberts, Ribosome Inactivating Proteins of Plants, 2 Seminars in Cell Biology 15–22 (1991). The type II RIPs are potent toxins, the best known of which is ricin. As used herein, "type II ribosome-inactivating proteins" or "type II RIPs" means two-chain N-glycosidases that cleave the N-glycosidic bond of adenine in a specific ribosomal RNA sequence, wherein the two chains are an A chain, which possesses the N-glycosidase activity, and a B chain, which comprises a galactose-specific lectin domain that binds to cell surfaces. Ricin is the prototypical type II ribosome-inactivating protein, but other such type II RIPs include abrin (from *Abrus precatrius*), modeccin (from *Adenia digtata*), viscumin (from *Viscum album*), and volkensin (from *Adenia volkensii*). C. H. Hung et al., Cloning and Expression of Three Abrin A-chains and Their Mutants Derived by Site-specific Mutagenesis in *Escherichia coli*, 219 Eur. J. Biochem. 83–87 (1994); K. A. Wood et al., Preproabrin: Genomic Cloning, Characterisation and the Expression of the A-chain in *Escherichia coli*, 198 Eur. J. Biochem. 723–732 (1991); C. H. Hung et al., Primary Structure of Three Distinct Isoabrins Determined by cDNA Sequencing: Conservation and Significance, 229 J. Mol. Biol. 263–267 (1993); GenBank accession numbers X76644, X76720, X76721, X76722, X54873, X54872, X55667, A58957; International Application publication no. W09701636. As used herein, "ricin A chain" means an N-glycosidase of about 32 kDa that digests and inactivates 26S and 28S ribosomal RNA by cleavage of a specific adenine residue located within a highly conserved region of the 26S and 28S ribosomal RNA, as is well known in the art. As used herein, "ricin B chain" means a galactose/N-acetylgalactosamine-binding lectin of about 34 kDa. SEQ ID NO:1 shows a DNA encoding preproricin and translation product thereof, wherein the signal peptide comprises amino acid residues −24 to −1, the A chain comprises amino acid residues 1 to 267, the linker peptide comprises amino acid residues 268 to 279, and the B chain comprises amino acid residues 280 to 541. This sequence is incomplete at the 5' end (L. M. Roberts, J. W. Tregear, J. M. Lord, Molecular Cloning of Ricin, 7 Targeted Diagn Ther 81–97 (1992)) and the entire sequence is given in SEQ NO. 2 and SEQ NO. 3, which follows. SEQ ID NO:2 and SEQ ID NO:3 show other DNAs encoding preproricin and their translation products thereof wherein the signal peptides comprise amino acid residues 35 to −1, the A chains comprise amino acid residues 1 to 267, the linker peptides comprise amino acid residues 268 to 279, and the B chains comprise amino acid residues 280 to 541. Preferred ricin A chains and ricin B chains include the peptides having the amino acid sequences identified as SEQ ID NO:1, SEQ ID NO:2, SEQ ID NO:3, and biologically functional equivalents thereof. These functional equivalents include any two-subunit, proteolytically activatable, N-glycosidase toxins that inactivate ribosomes, i.e., type II ribosome-inactivating proteins. Such functional equivalents of the ricin A chain, for example, retain functionality in digesting ribosomal RNA although they may be truncations, deletion variants, or substitution variants of the ricin A chain portions of SEQ ID NO:1, SEQ ID NO:2, or SEQ ID NO:3 or include additional amino acid residues attached thereto. Functional equivalents of the ricin A chain may also be derived from any other type I or type II ribosome inactivating protein. Functional equivalents of the ricin B chain, for example, (a) retain functionality of binding to galactose residues on the surface of cells although they may be truncations, deletion variants, or substitution variants of the ricin B chain portions of SEQ ID NO:1, SEQ ID NO:2, or SEQ ID NO:3 or include additional amino acid residues attached thereto; (b) retain functionality for inhibiting activity of the ricin A chain; (c) or both. Carbohydrate moieties may optionally be attached to the A or B chains.

As mentioned above, changes may be made in the structure of the type II ribosome-inactivating protein A chain or B chain while maintaining the desirable N-glycosidase or galactose-binding characteristics thereof. For example, certain amino acid residues may be substituted for other amino acid residues in a protein structure without appreciable loss of activity. Since it is the interactive capacity and nature of a protein that defines that protein's biological functional activity, certain amino acid sequence substitutions can be made in a peptide's sequence and nevertheless obtain a protein with like properties. It is thus contemplated that various changes may be made in the sequence of a type II ribosome-inactivating protein A chain or B chain without appreciable loss of its biological utility or activity.

It is also well understood by the skilled artisan that inherent in the definition of a biologically functional equivalent protein or peptide is the concept that there is a limit to the number of changes that may be made within a defined portion of the molecule and still result in a molecule with an acceptable level of equivalent biological activity. It is also well understood that where certain residues are shown to be particularly important to the biological or structural properties of a protein or peptide, e.g. residues in active sites, such residues may not generally be exchanged. Amino acid substitutions are generally based on the relative similarity of the amino acid side-chains relative to, for example, their hydrophobicity, hydrophilicity, charge, size, and the like. An analysis of the size, shape, and type of the amino acid side-chains reveals, for example, that arginine, lysine, and histidine are all positively charged residues at neutral pH; that alanine, glycine, and serine are all similar in size; and that phenylalanine, tryptophan, and tyrosine all have a generally similar shape. Therefore, based upon these considerations, the following conservative substitution groups or biologically functional equivalents have been defined:(a) Cys; (b) Phe, Trp, Tyr; (c) Gln, Glu, Asn, Asp; (d) His, Lys, Arg; (e) Ala, Gly, Pro, Ser, Thr; and (f) Met, Ile, Leu, Val. M. Dayhoff et al., Atlas of Protein Sequence and Structure (Nat'l Biomed. Res. Found., Washington, D.C., 1978). Based on similar considerations, another grouping of amino acids is as follows: (a) Pro; (b) Ala, Gly; (c) Ser, Thr; (d) Asn, Gln; (e) Asp, Glu; (f) His; (g) Lys, Arg; (h) Cys; (i) Ile, Leu, Met, Val; and (j) Phe, Trp, Tyr. M. Jimenez-Montano & L. Zamora-Cortina, Evolutionary Model for the Generation of Amino Acid Sequences and its Application to the Study of Mammal Alpha-hemoglobin Chains, Proc. VIIth Int'l Biophysics Congress, Mexico City (1981).

To effect more quantitative changes, the hydropathic index of amino acids may be considered. Each amino acid has been assigned a hydropathic index on the basis of its hydrophobicity and charge characteristics, which are as follows: isoleucine (+4.5); valine (+4.2); leucine (+3.8); phenylalanine (+2.8); cysteine (+2.5); methionine (+1.9); alanine (+1.8); glycine (0.4); threonine (0.7); serine (0.8); tryptophan (0.9); tyrosine (1.3); proline (1.6); histidine (3.2); glutamate (3.5); glutamine (3.5); aspartate (3.5); asparagine (3.5); lysine (3.9); and arginine (4.5).The importance of the hydropathic amino acid index in conferring interactive biological function on a protein is generally understood in the art. J. Kyte & R. Dooliffle, A Simple Method for Displaying the Hydropathic Character of a Protein, 157 J. Mol. Biol. 105–132 (1982). It is known that certain amino acids may be substituted for other amino acids having a similar hydropathic index or score and still retain a similar biological activity. In making changes based on the hydropathic index, the substitution of amino acids whose hydropathic indices are within ±2 is preferred, within ±1 is particularly preferred, and within ±0.5 is even more particularly preferred.

It is also understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0); glutamate (+3.0±1); serine (+0.3); asparagine (+0.2); glutamine (+0.2); glycine (0); threonine (0.4); proline (0.5±1); alanine (0.5); histidine (0.5); cysteine (1.0); methionine (1.3); valine (1.5); leucine (1.8); isoleucine (1.8); tyrosine (2.3); phenylalanine (2.5); tryptophan (3.4).

In making changes based upon similar hydrophilicity values, the substitution of amino acids whose hydrophilicity values are within±2 is preferred, within ±1 is particularly preferred, and within±0.5 is even more particularly preferred.

As used herein, "viral protease" and similar terms mean proteases coded for by viral nucleic acids and expressed in virus-infected cells. For example, all known human retroviruses encode their own proteases. E.g., R. A. Katz & A. M. Skalka, The Retroviral Enzymes, 63 Annu. Rev. Biochem. 133–173 (1994); K. Von der Helm, Retroviral Proteases: Structure, Function and Inhibition from a Non-anticipated Viral Enzyme to the Target of a Most Promising HIV Therapy, 377 Biol. Chem. 765–774 (1996). Retroviral proteases cleave a polyprotein precursor into a reverse transcriptase, capsid proteins, and other processed products. A variety of other viruses also encode their own proteases, including herpesviruses, hepatitis C viruses, rhinoviruses, and picornaviruses. A. K. Patick & K. E. Potts, Protease Inhibitors as Antiviral Agents, 11 Clin. Microbiol. Rev. 614–627 (1998); B. D. Korant, Viral Proteases: An Emerging Therapeutic Target, 8 Crit. Rev. Biotechnol. 149–157 (1988).

As used herein, "human immunodeficiency virus protease cleavage site" and similar terms mean peptides that are digested by HIV protease. HIV-1 and HIV-2 proteases, although not identical, both cleave a viral GAG precursor protein of HIV-2 at two very different sites to yield the same products. J. C. Wu et al., Synthetic HIV-2 Protease Cleaves the GAG Precursor of HIV-1 with the Same Specificity as HIV-1 Protease, 277 Arch. Biochem. Biophys. 306–311 (1990). One such site in the GAG precursor is Val-Ser-Gln-Asn-Tyr-Pro-Ile-Val-Gln-Asn (type 1 cleavage site wherein cleavage occurs between the tyrosine and proline residues; SEQ ID NO:4). The second site is Ser-Ala-Thr-Ile-Met-Met-Gln-Arg-Gly-Asn (type 2 cleavage site wherein cleavage occurs between the two methionine residues, SEQ ID NO:11). There are many different sequences cleaved by HIV-1 protease, which generally fall into one of two types exemplified by these two sites: type 1 having Tyr(Phe)-Pro- and type 2 having hydrophobic residues (excluding proline) at the site of cleavage. J. Tözsér et al., Studies on the Symmetry and Sequence Context Dependence of the HIV-1 Proteinase Specificity, 272 J. Biol. Chem. 16807–16814 (1997). This article by Tözsér et al. goes on to conclude that classification of retroviral cleavage sites into two types is an oversimplification and the strong sequence context dependence also raises difficulties for predicting cleavage sites. While the variability of sequences cleaved by HIV protease makes it difficult to predict cleavage sites, models have been successfully generated for the purpose of predicting these sites. K. C. Chou, A Vectorized Sequence-coupling Model for Predicting HIV Protease Cleavage Sites in Proteins, 268 J. Biol. Chem. 16938–16948 (1993); K. C. Chou, Prediction of Human Immunodeficiency Virus Protease Cleavage Sites in Proteins, 233 Anal. Biochem. 1–14 (1996). Proteases from HIV-1 and HIV-2 recognize and cleave the same two types of sequences, although not necessarily the same sequences with the same cleavage efficiencies. Thus, it is possible to construct a therapeutic agent useful for both forms of the virus. HIV-1 is the form prevalent in the Western world, while HIV-2 is typically found in West African patients with AIDS. However, HIV-1 is likely to cause AIDS in West African patients as well.

As used herein, "peptide" means peptides of any length and includes proteins. The terms "polypeptide" and "oligopeptide" are used herein without any particular intended size limitation, unless a particular size is otherwise stated.

As used herein, "carbohydrate" means carbohydrate monomers, oligomers, and polymers. There is no particular intended size limitation with respect to carbohydrate oligomers or polymers unless a particular size is otherwise stated.

As used herein, "lectin" means a class of proteins of nonimmunological origin that binds carbohydrates. The scope of lectins that can be used according to the present invention is limited only by functionality, i.e., binding to carbohydrates and/or inhibiting activity of a protein synthesis inactivating toxin to which it is fused. Segments or portions of lectins are also to be considered within the scope of the term "lectin" provided that such segments or portions retain the carbohydrate-binding and/or toxin-inhibiting function. Representative lectins that can be used according to the present invention include the following: abrin or jequirity bean (*Abrus precatorius*), asparagus pea or lotus or winged pea (*Tetragonolobus purpureas*), avocado (*Persea americana*), bitter pear melon (*Momordica charantia*), broad bean (*Vicia faba*), camels foot tree (*Bauhinia purpurea*), castor bean (*Ricinus communis*), chick pea (*Cicer arietinum*), Mozambique cobra (*Naja mocambique mocambique*), Thailand cobra (*Naja naja laculbia*), concanavalin A or jack bean (*Canavalia ersiformis*), Israel coral tree (*Erythina oxaliodendron*), daffodil (*Narcissus pseudonarcissus*), eel (*Anguilla anguilla*), elderberry (*Sambucus nigra*), furze or gorse (*Ulex europaeus*), green marine algae (*Cocleum fragile*), hairy vetch (*Vicia villosa*), horse gram (*Dolichos biflorus*), horseshoe crab or limulin (*Limulus polyphemus*), jacalin (*Artocarpus integrifolia*), Japanese wisteria (*Wisteria floribunda*), jimson weed or thorn apple (*Datura stramonium*), Scotch laburnum (*Laburnum alpinum*), lentil (*Lens culinaris*), lima bean (*Phaseolus limensis*), European mistletoe or viscumin (*Viscum album*), mung bean (*Vigna radiata*), mushroom (*Agaricus bisporus*), Osage orange (*Maclura pomifera*), pagoda tree (*Sophora japonica*), pea (*Pisum sativum*), peanut (*Arachis hypogaea*), pokeweed (*Phytolacca americana*), potato (*Solanum tuberosum*), red kidney bean (*Phaseolus vulgaris*), red marine algae (*Plifola plumosa*), Roman snail (*Helix porrata*), scarlet runner bean (*Phaseolus coccineus*), Scotch broom (*Cytisus scoparius*), Siberian pea tree (*Caragana arborescens*), snail-edible (*Helix pomatia*), snail-garden (*Helix aspersa*), snowdrop (*Galanthus nivalis*), soybean (*Glycine max*), spindle tree (*Euonymus europaeus*), sweet pea (*Lathyrus odoratus*), tomato (*Lycopersicon esculentum*), wheat germ (*Triticum vulgaris*), winged bean (*Psophoramus beliagonolobus*). Preferred lectins include the B chains of type II RIPS, such as ricin, abrin, modeccin, viscumin, and volkensin. Additional preferred lectins include tora-mame lectin (from *Phaeolus vulgaris*), phytohemagglutinin (PHA), wheat germ agglutinin, achatinin H, and *Vicia villosa* lectin. Still additional preferred lectins include lectins that bind to T lymphocytes, including mistletoe lectin, *Phaseolus vulgaris* leucoagglutinin, and lectins from *Bandeiraea simplicifolia* BS-I, *Bauhinia purpurea, Glycine max, Lycopersicon esculentum, Triticum vulgaris, Canavalia ensiformis, Lens culinaris, Phaseolus coccineus,* and *Wisteria floribunda*. Further additional preferred lectins include lectins that bind to sulfated carbohydrates, such as L-selectin and human galectin 1. Still further preferred lectins include lectins that bind to HIV gp120, including concanavalin A, wheat germ agglutinin, *Lens culinaris* agglutinin, *Vicia faba* agglutinin, *Pisum sativum* agglutinin, and phytohaemagglutinin. Another group of preferred lectins include the B subunits of Shiga and Shiga-like toxins (SLTs), such as the B chains of Shiga toxin, SLT-I, SLT-HI, SLT-IIv, and SLT-2e. Still other preferred lectins include jacalin, mannose binding proteins (e.g., concanavalin A), and maltose binding protein.

As used herein, a "pharmaceutically acceptable" component is one that is suitable for use with humans and/or animals without undue adverse side effects (such as toxicity, irritation, and allergic response) commensurate with a reasonable benefit/risk ratio. Such materials are pharmaceutically acceptable in that they are nontoxic, do not interfere with drug delivery, and are not for any other reasons biologically or otherwise undesirable.

As used herein, "effective amount" means an amount of a drug or pharmacologically active agent that is nontoxic but sufficient to provide the desired local or systemic effect and performance at a reasonable benefit/risk ratio attending any medical treatment.

As used herein, "administering" and similar terms mean delivering the composition to the individual being treated such that the composition is capable of being circulated systemically to the parts of the body where the viral protease-sensitive linker can be digested by the viral protease, thus cleaving a peptide bond in a linker that connects the type II ribosome-inactivating protein A chain and the type II ribosome-inactivating protein B chain. After such digestion, however, the A chain and the B chain will still be coupled to each other by a disulfide bond. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients or carriers include, for example, water, saline, dextrose, glycerol, ethanol, and the like; and if desired, minor amounts of auxiliary substances such as wetting or emulsifying agents, buffers, and the like can be added. Other carriers can be used and are well known in the art.

In its most basic embodiment, the present invention comprises a composition and method of use thereof, wherein the composition comprises a type II ribosome-inactivating protein precursor protein, such as proricin, wherein the natural linker is replaced with a viral-protease-cleavable linker. In an especially preferred embodiment of the invention, the natural linker is replaced with an HIV-protease-cleavable linker. Generally, there are two types of sequences cleaved by HIV proteases, which can be identified with some predictability. In certain embodiments, a major advantage of, for example, a proricin variant over typical immunotoxins is that cells in early stages of infection can be killed, thus preventing HIV replication.

Targeting molecules can be added to various sites on the proricin-based agent in addition to or for replacing the targeting activity of the B chain. Targeting molecules include, but are not limited to, CD4 and derivatives thereof; antibodies such as anti-gp120, anti-gp41, and the like; IL-2 segments; gp120 segments; gag segments; fatty acid or other hydrophobic substituents; and mannose-containing carbohydrate moieties. Especially preferred targeting molecules include gp120 segments and fatty acid or other hydrophobic substituents. Fatty acid groups may permit direct translocation of the agent into cells, rendering the activity of the B chain unnecessary, even though the presence of the B chain or a segment thereof would remain important so that the A chain would be inactive until proteolytically activated by HIV protease. An alternative mechanism for proteolytic activation involves an adenine or similar group attached to an HIV-protease-cleavable extension linker on the A chain, which will inhibit A chain activity until cleaved by HIV protease.

A major advantage of the present invention is that the antiviral agent is activated in viral particles or early-stage infected cells, killing the cells upon infection and effectively preventing the integration of the viral genome into the host genome and preventing the latency/rebound problem. Another major advantage in certain embodiments is that the present invention should be able to enter all HIV susceptible cells, not just cells known to act as host cells for the virus. Moreover, the agent remains inert in a cell until degraded therein, unless the cell is infected with the virus, wherein the viral protease activates the agent.

Human immunodeficiency virus (HIV) is representative of viruses that encode their own protease enzymes that cleave specific sites on viral proteins during the replication process. J. Gatlin et al., Regulation of Intracellular Human Immunodeficiency Virus Type-1 Protease Activity, 244 Virology 87–96 (1998). Examples of other protease-encoding viruses are yellow fever virus and tick-borne encephalitis virus. T. J. Chambers et al., Evidence that the N-terminal Domain of Nonstructural Protein NS3 from Yellow is Fever Virus is a Serine Protease Responsible for Site-specific Cleavages in the Viral Polyprotein, 87 Proc. Nat'l Acad. Sci. USA 8898–8902 (1990); K. V. Pugachev et al., Site-directed Mutagenesis of the Tick-borne Encephalitis Virus NS3 Gene Reveals the Putative Serine Protease Domain of the NS3 Protein, 328 FEBS Lett. 115–118 (1993). Vaccinia virus, which is so closely related to the smallpox virus that it was used as the basis for a vaccine against smallpox, apparently uses a protease specifically located within infected cells, R. M. L. Buller et al., Poxvirus Pathogenesis, 55 Microbiol. Rev. 80–122 (1991). The smallpox virus may use a similar protease.

The therapeutic agent described herein is based on type II ribosome-inactivating proteins, such as the protein toxin, ricin, and is generally applicable to viruses that encode site-specific proteases. From this point in the application, ricin will be used as a preferred example of a type II ribosome-inactivating protein, but it is intended that the scope of the invention include any protein synthesis inactivating toxin, as previously defined. As briefly reviewed above, ricin from castor beans comprises two subunits (A and B) connected by a disulfide bond, with carbohydrate chain(s) attached to each. J. M. Lord et al., Ricin: Structure, Mode of Action, and Some Current Applications, 8 FASEB J. 201–208 (1994); U.S. Pat. No. 5,622,838. The A subunit is an enzyme that cleaves a critical adenine residue from ribosomal RNA, thereby inactivating ribosomes. The B subunit is a lectin that binds to cell-surface galactose residues and also contributes to cellular internalization of the A-B toxin.

The rationale for using ricin-based therapeutic agents against HIV has been documented. M. G. C. T. Van Oijen et al., Rationale for Use of Immunotoxins in the Treatment of HIV-infected Humans, 5 J. Drug Target 75–91 (1997). Viruses appropriate the metabolic machinery of infected host cells to replicate themselves. By inactivating the machinery for protein synthesis, i.e., ribosomes, and thereby killing infected cells, selective ricin-based agents can prevent the replication of HIV. This strategy relies on is attaching targeting molecules that bind to infected cells. There are two major drawbacks to this approach. First, the viral antigens to which the targeting molecules bind may either be shed from the cell surfaces, J. M. Lord et al., supra, or occur on free viral particles, not just cell surfaces. Thus the intended targets (infected cells) are not efficiently destroyed. Second, the ricin-plus-targeting molecule conjugates must be administered in large doses, presumably because they are not ideally suited to the complex internalization pathway whereby ricin enters cells. B. M. Simmons et al., Mannose Receptor-mediated Uptake of Ricin Toxin and Ricin A Chain by Macrophages, 261 J. Biol. Chem. 7912–7920 (1986).

The present approach involves a modification of native proricin, which is the precursor of ricin that differs only in that the A and B subunits are connected by a peptide linker to form a continuous proricin peptide. Cleavage of proricin by a protease in castor beans (the source of ricin) yields the mature ricin protein. In the present invention, the naturally occurring peptide linker between the ricin A chain and the ricin B chain is replaced by an HIV-protease-cleavable site. Research results suggest that the A and B subunits are not normally separated until ricin reaches the cytoplasm, wherein the connecting disulfide bond is cleaved, J. P. Frenoy et al., Uptake of Injected $^{125}$I-ricin by Rat Liver In Vivo, 284 Biochem. J. 249–257 (1992); hence, a modified peptide linker connecting the A and B subunits should not interfere with cellular internalization of the protein variant. Indeed, internalization of this variant should be significantly more efficient than for immunotoxins that include targeting molecules.

These data strongly suggest that incorporating an HIV-protease-sensitive linker into proricin will produce an agent that selectively kills IRV-infected cells. Moreover, the proricin variant should work against both forms of the virus, HIV-1 and HIV-2, because it has been shown that HIV-2 protease cleaves the polyprotein precursor of HIV-1 with the same specificity as the HIV-1 protease. J. C. Wu et al., supra.

The proricin variant will bind to any cell that displays galactose residues on the cell surface. Another route for cellular uptake involves the mannose-containing carbohydrate chains attached to ricin as it is produced in castor beans and as it should be produced in a yeast cell host. These mannose groups are bound by mannose receptors on cell surfaces. B. M. Simmons et al., supra. Additional routes for cellular uptake could be engineered by attaching other sugar-binding lectins to the N-terminus of the ricin A chain or the C-terminus of the B chain. Other proteins have been attached to the N-terminus of the A chain without affecting ricin activity or internalization. B. Beaumelle et al., Ricin A Chain Can Transport Unfolded Dihydrofolate Reductase into the Cytosol, 272J. Biol. Chem. 22097–22102 (1997). Together, the many possible proricin variants will be able to enter virtually any cell type, but will be activated within and kill only virus-infected cells. Although the preferred embodiment of the present invention, described above, is designed to be activated in cells infected with HIV, it is also possible that other proteases present in the healthy human body might activate the proricin-based therapeutic agent. Therefore, it would be advantageous to increase the selectivity of the therapeutic agent still further. One solution for increasing selectivity would be to insert a linker containing a type 2 HIV-protease-cleavable site into proricin instead of a type 1 cleavable site. A protease found naturally in the human body may cleave one of the linker types, and activate the therapeutic agent. By changing the linker sequence, selectivity for HIV protease may be increased by avoiding linker cleavage by naturally occurring proteases.

A second solution to avoiding activation by nonspecific proteases is to insert amino acid residues into natural, exposed loops of A chain that are also found in the cleavable linker; such insertions cannot significantly reduce A chain activity. Also, these insertions cannot contain sequences cleavable by the viral protease. Therefore, if a host (i.e., human) protease can cleave the linker at a sequence also found in an A-chain loop insertion, the host protease will inactivate the ricin A chain and prevent destruction of uninfected cells.

Another solution to increasing selectivity is to attach a targeting moiety to the proricin variant. Five categories of targeting molecules are discussed herein: (1) Targeting to the surfaces of infected cells displaying viral proteins as the targets, e.g., gp 120. Such targeting molecules would include antibodies, viral proteins or portions thereof, and other proteins that bind to such viral components (e.g., CD4). Typical immunotoxins use this type of targeting molecule. (2) Targeting to injectable or susceptible cells. Molecules used for targeting include proteins that bind to CD4. (3) Targeting to virtually any cell. The ricin B chain binds to any cell displaying galactose residues. Mannose chains on ricin A and B chains could bind to mannose receptors. Fatty acids permit internalization into a variety of cells. Lectins other than the ricin B chain can also be used. (4) Intracellular targeting to the inner surface of the cell membrane for incorporation into viral particles. Fatty acids and/or segments of the GAG protein attached to the antiviral agent will promote this process. Any protein segment to which fatty acids are attached by enzymes in vivo can be fused to the antiviral agent. (5) Targeting with viral vectors, such as an HIV-based vector that would ultimately insert DNA encoding the antiviral agent into susceptible cells. One or more of these five different types of targeting strategies can be used.

A preferred targeting molecule for attachment to the modified proricin of the present invention is a molecule that targets the CD4 glycoprotein on cell surfaces or an antibody against an HIV envelope glycoprotein (S. H. Pincus, Therapeutic Potential of Anti-HIV Immunotoxins, 33 Antiviral Res. 1–9 (1996)). As is well-known in the art, attachment of HIV to cells involves the interaction of the HIV gp120 envelope glycoproteins with specific receptors on cell surfaces-the CD4 glycoprotein and members of the chemokine receptor family. R. Wyatt & J. Sodroski, The HIV-1 Envelope Glycoproteins: Fusogens, Antigens, and Immunogens, 280 Science 1884–1888 (1998). The CD4 glycoprotein is expressed on the surface of T lymphocytes, monocytes, dendritic cells, and brain microglia, the main target cells for primate immunodeficiency viruses in vivo. Use of CD4 protein or a derivative thereof as a targeting molecule would cause the present invention to bind surface-exposed pg120 and enter HIV-infected cells and cause inactivation of ribosomes in such cells, thus destroying the ability of the cells to produce new HIV proteins. However, this approach would only target cells in the late stage of infection that are expressing viral proteins on the cell surface. The problem at that point is that the viral genome has already been incorporated into the host cell genome. If viral particles are not being actively produced and their proteins displayed on the cell surface, then the cell will avoid the toxic effects of the CD4-based proricin variant. The virus could rebound at a later date upon cellular activation. G. Mathe, The Kinetics of Cancer Cells and of HIV1: The Problems of Cell and Virus Rebounds and of Latency, 52 Biomed. Pharmacother. 413–420 (1998).

HIV infections of central nervous system (CNS) cells can involve galactosyl ceramide as a receptor, enabling virus entry by a CD4-independent pathway. S. H. Pincus & V. V. Tolstikov, supra. Furthermore, infected CNS cells express little or no viral antigens on their surfaces. While these are not major sites of viral replication, such infected cells may represent a barrier to complete elimination of viral replication. Classical immunotoxins are poor candidates for attacking such cells. In contrast, the present embodiments of the invention involving fully functional B chain could readily bind to galactosyl ceramide, yet remain inactive unless HIV protease is encountered. Further, a compatible embodiment involving fatty acid attachment would facilitate crossing of the blood-brain barrier, which is a major impediment to the efficacy of immunotoxins.

Another targeting molecule would be a portion of interleukin-2 (IL-2) that binds to the high-affinity IL-2 receptors found on a subset of activated T-lymphocytes thought to be the main or sole site of HIV replication. However, it has not been demonstrated that this is the sole site in infected humans. S. H. Pincus, supra. Furthermore, the expression of IL-2 receptors on the surface of T cells appears to result from HIV infection or the binding of HIV gp120 to CD4 on the T-cell surface, R. W. Finberg et al., Selective elimination of HIV-1-infected Cells with an Interleukin-2 Receptor-specific Cytotoxin, 252 Science 1703–1705 (1991). Therefore, use of a segment of IL-2 on a classical immunotoxin would target infected cells, although T cells activated by non-HIV stimulants would also be eliminated. S. H. Pincus & V. V. Tolstikov, supra. However, infected cells targeted in this manner should be at an earlier stage of infection relative to cells targeted by immunotoxins containing CD4 segments or antibodies against viral proteins. A portion of IL-2 has been fused to diphtheria toxin as an anti-HIV "immunotoxin." R. W. Finberg et al., supra.

Since use of IL-2 as a targeting molecule on classical immunotoxins could result in destruction of uninfected cells and deleterious health effects, the protease activation mechanism of the present invention will be important to confer additional selectivity. A strategy for attacking viral latency (stable, dormant provirus integrated into host DNA) is to activate infected T cells to express IL-2 receptors and perhaps viral proteins by exposing patients to exogenous HIV gp120. H. Kornfeld, W. W. Cruikshank, S. W. Pyle, J. S. Berman. D. M. Center, Lymphocyte Activation by HIV-1 Envelope Glycoprotein, 335 Nature 6189 (1988). After several hours, treatment with a protease-activated therapeutic agent containing IL-2 would destroy infected cells. Without activation of the provirus, the therapeutic agent would likely be degraded in the cell before it could be activated. Alternatively, use of the carbohydrate-(galactose-) binding B chain or another lectin separately or as part of the toxin-based therapeutic agent could activate infected T cells. B. A. Sela et al., Lymphocyte Activation by Monovalent Fragments of Antibodies Reactive with Cell Surface Carbohydrates, 143 J. Exp. Med. 665–671 (1976); O. Closs et al., Stimulation of Human Lymphocytes by Galactose-specific Abrus and Ricinus Lectins, 115 J. Immunol. 1045–1048 (1975).

A better approach would be to kill infected cells at a very early stage of infection, i.e. before the integration of the viral genome. To do this would require a different targeting molecule. One possibility is attaching an octapeptide (or derivative thereof) from the HIV envelope glycoprotein gp120. C. B. Pert et al., Octapeptides Deduced from the Neuropeptide Receptor-like Pattern of Antigen T4 in Brain Potently Inhibit Human Immunodeficiency Virus Receptor Binding and T-cell Infectivity, 83 Proc. Nat'l Acad. Sci. USA 9254–9258 (1986). This short sequence is believed to play an important role in HIV attachment to cells. It could be incorporated into the proricin variant at its N-terminus or at another site in the variant. The receptor for this octapeptide is the T4 or CD4 protein. Entry of primate immunodeficiency viruses into the host cell involves the binding of the gp120 envelope glycoprotein to the CD4 glycoprotein, which serves as the primary receptor. P. D. Kwong et al., Structure of an HIV gp120 Envelope Glycoprotein in Complex with the CD4 Receptor and a Neutralizing Human Antibody, 393 Nature 648–659 (1998). This receptor is also located on membranes of cells in the human brain. Interestingly, patients with AIDS show neuropsychological deficits. This embodiment of the invention could thus enter any cells that attach to HIV particles, but would be activated only when HIV protease is present.

Other portions of viral proteins could also be fused to the proricin variant. One of these is a largely deglycosylated "gp 120 core" consisting of a truncated version of the native gp120 with mutations in some of the loops. P. D. Kwong et al., supra; R. Wyatt et al., The Antigenic Structure of the HIV gp120 Envelope Glycoprotein, 393 Nature 705–711 (1998). Several antigenic residues in gp120 interact with the CD4 protein. R. Wyatt et al., supra. Peptides based on these data can be fused to the proricin variant. Also, a short segment of the V3 loop of the gp120 protein can bind to "secondary" cell receptors. J. B. Ghiara et al., Crystal Structure of the Principal Neutralization Site of HIV-1,264 Science 82–85 (1994). This segment could be flanked by cysteine residues to form a disulfide bond in the genetically engineered variant and thereby stabilize the immunogenic secondary structure of the V3 loop segment. A. Zhang et al., A Disulfide-bound HIV-1 V3 Loop Sequence on the Surface of Human Rhinovirus 14 Induces Neutralizing Responses Against HIV-1, 380 Biol. Chem. 365–374 (1999).

Immunogenic peptides that represent epitopes on the HIV gag protein might also serve as targeting molecules. J. M. Claverie et al., T-immunogenic Peptides Are Constituted of Rare Sequence Patterns. Use in the Identification of T Epitopes in the Human Immunodeficiency Virus Gag Protein, 18 J. Eur. Immunol. 1547–1553 (1988). The gag segment will direct an agent that contains it to be incorporated into the virus particle forming at the inner surface of the plasma membrane. C. T. Wang et al., Sequence Requirements for Incorporation of Human Immunodeficiency Virus Gag-$^2$-galactosidase Fusion Proteins into Virus-like Particles, 59 J. Med. Virol. 180–188 (1999); M. Bryant & L. Ratner, Myristoylation-dependent Replication and Assembly of Human Immunodeficiency Virus 1, 87 Proc. Nat l Acad. Sci. USA 523–527 (1990). An appropriate segment may include the N-terminus of the Pr55gag protein, which is attached to myristic acid in vivo, thereby causing the myristylated protein to associate with the inner surface of the plasma membrane and the nascent virus particle.

Peptide targeting molecules can be coupled to the proricin variant by expression of a recombinant fusion protein, chemical synthesis and attachment, or any other suitable method known in the art. Such techniques for producing recombinant fusion proteins are well-known in the art, and are described generally in, e.g., J. Sambrook & D. Russell, Molecular Cloning: A Laboratory Manual (3d ed., 2001). Reagents useful in applying such techniques, such as restriction endonucleases and the like, are widely known in the art and commercially available from any of several vendors.

The activity of HIV protease is regulated such that it is minimal in the cytoplasm and most active inside the virus particle. J. Gatlin et al., supra. The activity in the cytoplasm may be sufficient to activate the proricin variant of this invention. This phenomenon of high activity in the viral particle, however, could be used to advantage to kill the cells upon infection, prior to integration of the viral DNA into the host DNA. By attaching fatty acid residues to the proricin variant, it would bind to the inner surface of the cell membrane and be incorporated into the budding virus particle just as fatty-acid-labeled viral proteins are directed to the membrane. M. Bryant & L. Ratner, supra. In this sense, the fatty acid is a targeting molecule. Hydrophobic groups other than fatty acids could provide the same function. Fatty acids could be incorporated by chemical treatment with fatty acyl halides or by coupling fatty acids to the proricin via carbodiimide chemistry. Upon secondary infection, when the virus containing the proricin variant fuses with the membrane of a new cell, it would release the HIV-proteaseactivated proricin variant into the cytoplasm, where the disulfide bond is reduced and the A chain is released, and thereby kills the cell before integration of the viral genome. It may be necessary to use an HIV-protease-cleavable linker that is not the optimal sequence for cleavage such that activation of the variant is promoted only within virus particles. A second advantage of using a fatty acylated proricin variant is that the fatty acids could promote cellular internalization of the therapeutic agent, V. Y. Alakhov et al., Increasing Cytostatic Effects of Ricin A Chain and *Staphylococcus aureus* Enterotoxin A through In Vitro Hydrophobization with Fatty Acid Residues, 12 Biotechnol. Appl. Biochem. 94–98 (1990), bypassing the complex internalization route for wild-type ricin involving the endoplasmic reticulum. This has been demonstrated with the ricin A chain. V. Y. Alakhov et al., supra.

Mannose residues on the ricin B chain may be required for the lectin binding activity. M. Westby et al., Preparation and Characterization of Recombinant Proricin Containing an Alternative Protease-sensitive Linker Sequence, 3 Bioconjug. Chem. 375–381 (1992). Therefore, a preferred embodiment of the invention involves making the proricin variant in a eukaryotic host, such as yeast, to provide the necessary glycosylation. The mannose residues are also targeting molecules and can direct native ricin to cells displaying mannose receptors, leading to cell intoxication. D. L. Newton et al., supra; B. M. Simmons et al., supra.

If one of the targeting molecules mentioned above is used, it may be possible to eliminate one or more of the galactose binding sites of the ricin B chain by point mutations, D. L. Newton et al., supra, or deletions. The mannose residues may also be eliminated by expression of a gene construct in a prokaryotic host or by enzymatic removal. However, at least one of the galactose binding sites appears to be required for effective cellular internalization of native ricin. D. L. Newton et al., supra. Leaving the galactose binding sites intact allows the possibility that nonspecific entry into cells would occur despite the incorporation of other targeting molecules. Intoxication, however, would still require that the cells expressed a protease that would cleave the modified proricin-based agent. The advantage of leaving one or both galactose binding sites intact is that the internalization of the agent into cells would be enhanced. Of course, adding fatty acid residues may allow direct cellular internalization of the agent and avoid the need for galactose binding sites.

Viral vectors could also be used to deliver a gene coding for this antiviral agent to human cells. HIV-based vectors capable of accomplishing this are known in the art. E.g., R. Zufferey et al., Self-inactivating Lentivirus Vector for Safe and Efficient In Vivo Gene Delivery, 72 J. Virol. 9873–9880 (1998); H. Miyoshi et al., Development of a Self-inactivating Lentivirus Vector, 72 J. Virol. 8150–8157 (1998). Such an HIV-based vector would have the nucleic acid coding for the antiviral agent of the present invention inserted into it. This vector containing the nucleic acid coding for the antiviral agent would then be administered to patients according to methods known in the art. A percentage of the cells in the body would become transduced with this construct and would thereafter continuously produce the antiviral agent. The antiviral agent would circulate in the blood, creating a condition similar to that created by injection of exogenous antiviral agent into the patient. The circulating antiviral agent could enter any HIV injectable cell, but would be activated and kill the cell only in the presence of HIV protease.

In still another embodiment of the invention, one of the termini of the ricin A chain is extended by means of making a fusion protein, then an adenine or adenine-like group is attached chemically. A cysteine residue may be incorporated into the extension to facilitate chemical attachment of the adenine group. The adenine-like group should not contain adenosine since the adenine moiety is likely to be cleaved from the ribose by the A chain. In this embodiment, the X (protease cleavable) linker is contained within the extension and the B chain is removed. The adenine residue would occupy the active site of the ricin A chain and inhibit activity. The extension linker would contain a cleavage site of an HIV protease. Upon cleavage, the linker/adenine would be separated and inhibition would be relieved, activating the ricin A chain. Adenine and pteroic acid, an adenine-like molecule, are known inhibitors of ricin. A. Pallanca et al., Uncompetitive Inhibition by Adenine of the RNA-N-glycosidase Activity of Ribosome-inactivating Proteins, 1384 Biochim. Biophys. Acta 277–284 (1998); J. D. Robertus et al., Structural Analysis of Ricin and Implications for Inhibitor Design, 34 Toxicon 1325–1334 (1996). It should be noted that there are two cysteine residues in the primary sequence of the ricin A chain that do not participate in a disulfide bond and are apparently not conserved among plant and bacterial ricin-like toxins. Y. Kitaoka, Involvement of the Amino Acids Outside the Active-site Cleft in the Catalysis of Ricin A Chain, 257 Eur. J. Biochem. 255–262 (1998). Thus, these two cysteine residues may not be essential to the activity of the ricin A chain. These cysteine residues could be mutated to other residues, leaving only the cysteine in the extension linker. 8-Adeninethiol could be coupled to this cysteine residue with, for example, a bismaleimide reagent. Pteroic acid could be coupled to an amine in the linker by carbodiimide chemistry. Other adenine-like molecules and attachment chemistries are possible and are well known in the art.

The gene for the proricin variant according to the present invention is preferably produced by amplifying the intron-free gene for preproricin in castor beans. The preproricin DNA sequence is known, e.g. F. I. Lamb et al., Nucleotide Sequence of Cloned cDNA Coding for Preproricin, 148 Eur. J. Biochem. 265–270 (1985); J. W. Tregear & L. M. Roberts, The Lectin Gene Family of Ricinus communis: Cloning of a Functional Ricin Gene and Three Lectin Pseudogenes, 18 Plant Mol. Biol. 515–525 (1992); K. C. Halling et al., Genomic Cloning and Characterization of a Ricin Gene from Ricinus communis, 13 Nucleic Acids Res. 8019–8033 (1985); L. M. Roberts et al., Molecular Cloning of Ricin, 7 Targeted Diagn. Ther. 81–97 (1992); JP 1985102188-A; U.S. Pat. No. 5,622,838. Methods for amplifying selected DNA segments, U.S. Pat. Nos. 4,683,195; 4,683,202; 4,800,159; 4,965,188; PCR Technology: Principles and Applications for DNA Amplification (H. Erlich ed., Stockton Press, New York, 1989); PCR Protocols: A guide to Methods and Applications is et al. eds, Academic Press, San Diego, Calif., 1990), and synthesizing oligonucleotides, S. A. Narang et al., 68 Meth. Enzymol. 90 (1979) (phosphotriester method); E. L. Brown et al., 68 Meth. Enzymol. 109 (1979) (phosphodiester method); U.S. Pat. Nos. 4,356,270; 4,458,066; 4,416,988; 4,293,652; N. D. Sinha et al., 24 Tetrahedron Lett. 5843 (1983); N. D. Sinha et al., 12 Nucl. Acids Res. 4539 (1984); N. D. Sinha et al., 15 Nucl. Acids Res. 397 (1987); N. D. Sinha et al., 16 Nucl. Acids Res. 319 (1988), are well known in the art. Methods for joining such amplified DNAs and synthetic DNAs are also well known in the art, e.g. J. Sambrook & D. Russell, Molecular Cloning: A Laboratory Manual (3d ed., 2001); T. Maniatis et al., Molecular Cloning: A Laboratory Manual (1982); F. Ausubel et al., Current Protocols in Molecular Biology (1987).

Next, the DNA encoding the preproricin variant containing the HIV protease site is cloned in an appropriate expression vector for expression in a suitable host cell, as is well known in the art. Methods for cloning in these vectors are well known in the art, e.g., Sambrook, supra; Maniatis, supra; Ausubel, supra. Such suitable host cells are preferably eukaryotic cells, but expression in prokaryotic cells is also intended to be within the scope of the present invention. Expression vectors for expression in eukaryotic cells, e.g., yeast, insect, and mammalian cells, and prokaryotic cells, e.g., bacterial cells, are well known in the art and are commercially available from numerous companies or from depositories such as the American Type Culture Collection. Such expression vectors generally contain the necessary promoters, transcription termination signals, translation initiation and termination signals, and the like for expression of the cloned DNA in the selected host cell. The cloned DNA is then expressed in a selected host transformed with the expression vector containing the variant preproricin DNA. Transformation of bacterial and eukaryotic cells is well known in the art and can be carried out by any appropriate method, such as calcium-dependent methods, heat shock, electroporation, and other effective methods and combinations thereof. The expressed protein is then purified, preferably by affinity of the ricin B chain for galactose-labeled agarose beads if the variant contains functional galactose binding sites of the B chain. Such affinity-based purification methods are also well known in the art.

Next, the purified proricin variant is tested for susceptibility to HIV protease and various other proteases to determine if the proricin variant is indeed selectively activated by HIV protease. As a first matter, the HIV protease should digest the proricin variant peptide, resulting in ricin A and B chains linked by a disulfide bond. The resulting ricin is chemically reduced and tested for ricin A chain activity against ribosomes using commercial in vitro translation kits.

The proricin variant containing the HIV protease site can be hydrophobized, as briefly described above. This modification has several advantages, including making it easier for the proricin variant to enter cells in vivo. Further, the hydrophobic agent coupled to the proricin variant has a tendency to direct the proricin variant to the inner surface of the cell membrane, as described above, where it can be incorporated into HIV particles during budding of the HIV particles through the cell membrane. Preferred hydrophobic agents include bile acids, sterols, and saturated and unsaturated fatty acids. Preferred bile acids include cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof. Preferred sterols include cholestanol, coprostanol, cholesterol, epicholesterol, ergosterol, ergocalciferol, and mixtures thereof. Preferred saturated and unsaturated fatty acids comprise about 4 to 20 carbon atoms, such as butyric acid, valeric acid, caproic acid, caprylic acid, capric acid, lauric acid, myristic acid, palmitic acid, stearic acid, oleic acid, linoleic acid, linolenic acid, eleostearic acid, and mixtures thereof. The hydrophobic agent can be coupled to the proricin variant by chemical conjugation or, in appropriate cases, by using enzymes. For example, an alkanoic acid can be coupled to the proricin variant by forming an amide bond between the carboxylic acid group of the alkanoic acid and an amino group of the proricin variant. The amino group can be the N-terminal amino group of the proricin variant and/or one or more of the $\mu$-amino groups of lysine residues. As is well known in the art, this reaction could be carried out chemically by activating the alkanoic acid by conversion to an acid chloride, and then reacting the acid chloride with the proricin variant to result in formation of the amide bond.

In still another embodiment of the present invention, a targeting moiety is coupled to the proricin variant. For example, a peptide targeting agent can be coupled to the proricin molecule either chemically or by recombinant DNA methodology. In some embodiments, the compositions are constructed by chemically conjugating the targeting moiety to the proricin variant. "Chemically conjugating" the targeting moiety to the proricin variant, as that term is used herein, means covalently bonding the targeting moiety to the proricin variant either directly or by way of a spacer moiety. Such spacer moieties can include heterobifunctional crosslinkers, such as are well known in the art. Peptide portions of the compositions of the present invention can be produced in a genetically engineered organism, such as *E. coli* or yeast, as a "fusion protein." That is, a hybrid DNA containing a sequence of nucleotides encoding the targeting moiety and the proricin variant can be constructed by recombinant DNA technology. This hybrid DNA can be inserted into an organism such that the "fusion protein" encoded by the hybrid DNA is expressed, as described above. The fusion protein can then be purified by standard methods, including affinity chromatography. If the targeting moiety is a relatively short peptide, such peptide can also be chemically synthesized. Methods for synthesis of peptides are well known in the art. E.g., R. B. Merrifield, Solid Phase Peptide Synthesis,32 Adv. Enzymol. Relat. Areas Mol. Biol. 221–96 (1969); R. B. Merrifield et al., 21 Biochemistry 5020–31 (1982) (solid phase peptide synthesis); Houghten, 82 Proc. Nat'l Acad. Sci. USA 5131–35 (1985) (solid phase peptide synthesis); Hunkapiller et al., 310 Nature 105–111 (1984).

EXAMPLE 1

In this example there is described an illustrative method for making a modified proricin according to the present invention. A DNA encoding modified preproricin is assembled from two DNA fragments amplified by PCR using two sets of primers containing the selected modifications. These primers were designed using the Lasergene program (DNASTAR Inc., Madison, Wis.). The template for the PCR reaction is cellular DNA isolated from castor bean; this is possible because the preproricin gene contains no introns. The resulting modified protein replaces the first 10 amino acid residues in the native proricin linker, which contains 12 amino acid residues, with the sequence Val-Ser-Gln-Asn-Tyr-Pro-Ile-Val-Gln-Asn (SEQ ID NO:4). This modified linker peptide (SEQ ID NO:12) is a substrate for the HIV protease, which digests the peptide between the tyrosine and proline residues. The nucleotide sequence coding for the altered amino acid residues (SEQ ID NO:5) was chosen using the codons that are most frequently used in baker's yeast, *Saccharomyces cerevisiae*. This nucleotide sequence contains a restriction endonuclease digestion site in the middle portion of the modified sequence. This site, CAATTG, is recognized by the enzyme MfeI, which has no other sites in the preproricin gene sequence. Thus, the strategy for making the modified preproricin gene is to PCR-amplify the entire modified preproricin gene in two segments that overlap in the region encoding the modified linker. The PCR primers for amplifying these fragments are SEQ ID NO:6 and SEQ ID NO: 7 for amplifying the 5' portion of the preproricin gene and SEQ ID NO: 8 and SEQ ID NO:9 for amplifying the 3' portion of the gene. After amplification, both fragments are digested with MfeI and then ligated together to produce a complete, modified preproricin coding sequence (SEQ ID NO:10).

Since bacteria do not properly glycosylate eukaryotic proteins, and the available evidence suggests that proper processing and glycosylation is required for stability, solubility, and galactose binding activity of the modified preproricin, M. Westby et al., supra, the modified preproricin gene is expressed in yeast. Yeast glycosylate and process such a protein provided that it contains a typical eukaryotic leader sequence. P. T. Richardson et al., The Expression of Functional Ricin B-chain in *Saccharomyces cerevisiae*, 950 Biochim. Biophys. Acta 385–394 (1988). Thus the upstream end of the amplified gene includes the entire coding sequence of preproricin instead of merely the coding sequence of the mature, processed protein (i.e., proricin). Although there are a large number of effective yeast expression vectors available in the art, in this example the modified preproricin gene is inserted in the yeast expression vector, pYES2, available commercially from Invitrogen (Carlsbad, Calif.). This vector contains origins of replication and selectable markers for replication and selection in both yeast and *E. coli*. In addition, this vector contains 10 unique restriction sites in its multiple cloning site, the large majority of which do not occur in the modified preproricin gene sequence. The SacI and XhoI sites were chosen for cloning and expression of the preproricin gene. Thus, a SacI site is engineered into the 5' end of the gene using the primer of SEQ ID NO:6, and an XhoI site is engineered into the 3' end of the gene using the primer of SEQ ID NO:9. Therefore, after PCR amplification, besides being digested with MfeI, each fragment is digested with SacI or XhoI, as appropriate; the pYES2 vector is digested with both SacI and XhoI; and the digested preproricin gene fragments and pYES2 vector are mixed and ligated according to methods well known in the art. The sticky ends direct how the various fragments are joined, and experience shows that the vast majority of recovered circular plasmids have the desired structure.

After ligation, the ligation mixture is used to transform competent *E. coli* cells according to methods well known in the art. Transformed cells are selected using the ampicillin marker on the pYES2 vector. Plasmid minipreps are prepared from several randomly selected colonies. Colonies containing the desired plasmid are identified by the size of the plasmid compared to the vector and by the presence of DNA fragments of the correct size following digestion with SacI and MfeI and with MfeI and XhoI. A large preparation of the plasmid containing the correct fragments is then prepared according to methods well known in the art and used to transform an appropriate yeast host strain (e.g., INVSc1, Invitrogen) using the spheroplast procedure or by making yeast cells competent using proprietary reagents (Invitrogen). Transformed cells are selected using the ura3 marker on the pYES2 vector, and then selected cells are grown and expression of the modified proricin is induced by addition of galactose to the medium. After further growth for expression, the cells are harvested, washed, lysed by agitation with glass beads or by sonication, and a cell-free extract is prepared. The modified proricin is purified from this extract using its galactose-binding activity by chromatography on an affinity column containing either bound galactose or lactose, similar to the way in which recombinant fusion proteins containing the maltose binding protein are purified. Kellerman & Ferenci, 90 Methods in Enzymology 459–463 (1982). Such columns are available commercially, such as from Sigma Chemical Co. (St. Louis, Mo.). The bound protein is specifically eluted from the column with galactose or a galactose-containing molecule.

EXAMPLE 2

In this example, the HIV-protease-susceptible linker SEQ ID NO:13 is substituted for SEQ ID NO:12 (see Example 1) using methods well known in the art.

EXAMPLE 3

In this example, a polynucleotide encoding a fusion peptide, comprising yeast alpha factor leader-ricin A chain-HIV protease cleavable linker-ricin B chain containing a phe to gly mutation at the extreme C-terminus-stop signal, was inserted in the pYES2 yeast expression vector. The alpha factor leader allows secretion and translocation to the endoplasmic reticulum where glycosylation can occur. The phe to gly mutation allows for creation of a unique restriction site and exposes hydrophobic residues on the A chain, according to published crystal structure data. E. Rutenber & J. D. Robertus, Structure of Ricin B-chain at 2.5 Å Resolution, 10 Proteins 260–269 (1991).

EXAMPLE 4

In this example, a polynucleotide encoding a fusion peptide, comprising: [maltose binding protein-factor Xa site-DP178-ricin A chain-HIV protease cleavable linker-truncated ricin B chain-repeat of hydrophobic val-ser-ile-leu-ile-pro-ile-ile-ala-leu-met-val (SEQ ID NO:14) (duplicated from the C-terminus of the A chain)stop signal], was inserted in the pMALp2X *E. coli* expression vector. DP178 is a section of the gp41 ectodomain involved in viral fusion to host cells. It is about 40 amino acid residues in length and has been shown to inhibit infectivity. The truncated B chain includes the first cys residue and about an additional 7–8 residues. The hydrophobic repeat is intended to facilitate translocation across membranes, such as the lumen of the endoplasmic reticulum to the cytosol.

EXAMPLE 5

In this example, a gly-ala-arg-ala-ser (SEQ ID NO:17) myristylation signal sequence (from HIV gag protein) was inserted between the factor Xa cleavage site and DP178 of the construct of Example 4. The myristylation sequence should promote attachment of fatty acids in vivo, and should direct the therapeutic agent to an intracellular site of nascent virus particles and HIV protease activity.

EXAMPLE 6

In this example, an "L domain" (pro-pro-pro-pro-tyr, SEQ ID NO:15) and an ER lumen retention signal (lys-asp-glu-leu, SEQ ID NO:16) are inserted after the repeat of the hydrophobic sequence from the C-terminus of the A chain of the construct of Example 5. The short L domain sequence has been fused to proteins other than the viral proteins in which it naturally occurs. It promotes the release of viral proteins from membranes by an unknown mechanism. The ER lumen retention signal has been shown to enhance toxicity of the ricin A chain when fused to the C-terminus thereof.

EXAMPLE 7

In this example, the procedure of Example 3 was carried out except that a single domain ricin B chain was substituted for the ricin B chain. The single domain ricin B chain contains no glycosylation sites, but has both galactose binding sites.

EXAMPLE 8

Three constructs were prepared for evaluating the concept that highly truncated ricin B chain can inhibit ricin A chain activity and thus permit an HIV-protease-dependent activation mechanism. These constructs were designed for cytosolic expression in yeast, and were expected to kill the cells if the A chain was in active form. Construct A comprises a fusion of ricin A chain-HIV protease cleavable linker-full ricin B chain, in pYES2. Construct B comprises a fusion of ricin A chain-HIV protease cleavable linker truncated at the expected cleavage site, in pYES2. Construct C comprises a fusion of ricin A chain-HIV protease cleavable linker-highly truncated B chain-repeat of hydrophobic sequence (SEQ ID NO:14) duplicated from C-terminus of A chain, in pYES2.

Yeast containing plasmids A, B, or C were streaked onto semi-solid media lacking uracil and containing glucose, raffinose, or raffinose+galactose. The pYES2-based plasmids were maintained in the cells because they confer the ability to grow in the absence of uracil. After incubation for 5 days at 30° C., the amount of growth was noted. Glucose permits growth but represses synthesis of the encoded agent. Raffinose permits growth but neither represses nor induces synthesis. Galactose alone does not permit growth, but induces synthesis of the encoded agent. Growth was obtained in all cases except for cell containing plasmid B on raffinose+galactose, wherein there was no growth. These results suggest that cleavage at the expected site by HIV protease results in activation of the ricin A chain and cell death. Further, the B chain may be highly truncated, albeit with a hydrophobic extension, and still inhibit A chain activity.

We claim:

1. A composition comprising a compound represented by the formula $(T_m\text{-}A\text{-}X\text{-}B)\text{-}H_n$ or $(A\text{-}X\text{-}B\text{-}T_m)\text{-}H_n$, wherein A is a protein synthesis inactivating toxin that is inactive until X is digested;

X is a peptide susceptible to digestion by a viral protease;
B is a segment of a lectin, T is a targeting moiety, H is a hydrophobic agent, m is 0 or an integer of at least 1, and n is 0 or an integer of at least 1.

2. The composition of claim 1 wherein said viral protease is from a retrovirus, picornavirus, rhinovirus, hepatitis C virus, or herpesvirus.

3. The composition of claim 1 wherein A is a ricin A chain and B is a segment of a ricin B chain.

4. The composition of claim 1 wherein X is a member selected from the group consisting of SEQ ID NO:12 and SEQ ID NO: 13.

5. The composition of claim 1 wherein said targeting moiety is a member selected from the group consisting of antigen-binding proteins, viral surface components and segments thereof, proteins that bind viral surface components, growth factors, lectins, and carbohydrates.

6. The composition of claim 5 wherein said targeting moiety is a member selected from the group consisting of antibodies against gp120, antibodies against gp41, and the CD4 protein or segments thereof.

7. The composition of claim 5 wherein said targeting moiety is an antigen-binding protein that binds the CD4 glycoprotein.

8. The composition of claim 7 wherein the protein that binds the CD4 glycoprotein is gp120 or a segment thereof.

9. The composition of claim 1 wherein said targeting moiety is a GAG protein segment.

10. The composition of claim 1 wherein said hydrophobic agent is a member selected from the group consisting of bile acids, sterols, and saturated and unsaturated fatty acids.

11. The composition of claim 10 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

12. The composition of claim 10 wherein said hydrophobic agent is a sterol selected from the group consisting of cholestanol, coprostanol, cholesterol, epicholesterol, ergosterol, ergocalciferol, and mixtures thereof.

13. The composition of claim 10 wherein said hydrophobic agent is a saturated or unsaturated fatty acid comprising about 4 to 20 carbon atoms.

14. The composition of claim 13 wherein said saturated or unsaturated fatty acid is a member selected from the group consisting of butyric acid, valeric acid, caproic acid, caprylic acid, capric acid, lauric acid, myristic acid, palmitic acid, stearic acid, oleic acid, linoleic acid, linolenic acid, eleostearic acid, and mixtures thereof.

15. The composition of claim 1 further comprising a pharmaceutically acceptable carrier admixed with the compound.

16. The composition of claim 1 wherein A, B, or both are from ADP-ribosyltransferases.

17. The composition of claim 1 wherein T comprises a myristylation signal sequence.

18. A composition comprising a compound represented by the formula A-X-B, wherein A is a protein synthesis inactivating toxin that is inactive until X is digested; X is a peptide susceptible to digestion by a viral protease; and B is a segment of a lectin.

19. The composition of claim 18 wherein said viral protease is from a retrovirus, picornavirus, rhinovirus, hepatitis C virus, or herpesvirus.

20. The composition of claim 18 wherein X is a member selected from the group consisting of SEQ ID NO:12 and SEQ ID NO: 13.

21. The composition of claim 18 wherein A is a ricin A chain and B is a segment of a ricin B chain.

22. The composition of claim 18 further comprising a pharmaceutically acceptable carrier admixed with the compound.

23. A composition comprising a compound represented by the formula A-X-B, wherein A is a ricin A chain that is inactive until X is digested; X is a peptide susceptible to digestion by a viral protease and is a member selected from the group consisting of SEQ ID NO:12 and SEQ ID NO:13; and B is a segment of a ricin B chain.

24. The composition of claim 23 further comprising a pharmaceutically acceptable carrier admixed with the compound.

25. A composition comprising a compound represented by the formula $(T_m\text{-}A\text{-}X\text{-}B)\text{-}H_n$ or $(A\text{-}X\text{-}B\text{-}T_m)\text{-}H_n$, wherein A is a protein synthesis inactivating toxin that inactive until X is digested; X is a peptide susceptible to digestion by a viral protease; B is a lectin or a segment thereof, T is a targeting moiety, H is a hydrophobic agent, m is 0 or an integer of at least 1, and n is an integer of at least 1.

26. The composition of claim 25 wherein said viral protease is from a retrovirus, picornavirus, rhinovirus, hepatitis C virus, or herpesvirus.

27. The composition of claim 25 wherein A is a ricin A chain and B is a ricin B chain.

28. The composition of claim 25 wherein X is a member selected from the group consisting of SEQ ID NO:12 and SEQ ID NO: 13.

29. The composition of claim 25 wherein said targeting moiety is a member selected from the group consisting of antigen-binding proteins, viral surface components and segments thereof, proteins that bind viral surface components, growth factors, lectins, and carbohydrates.

30. The composition of claim 29 wherein said targeting moiety is a member selected from the group consisting of antibodies against gp120, antibodies against gp41, and the CD4 protein or segments thereof.

31. The composition of claim 29 wherein said targeting moiety is an antigen-binding protein that binds the CD4 glycoprotein.

32. The composition of claim 31 wherein the protein that binds the CD4 glycoprotein is gp120 or a segment thereof.

33. The composition of claim 25 wherein said targeting moiety is a GAG protein segment.

34. The composition of claim 25 wherein said hydrophobic agent is a member selected from the group consisting of bile acids, sterols, and saturated and unsaturated fatty acids.

35. The composition of claim 34 wherein said hydrophobic agent is a bile acid selected from the group consisting of cholic acid, deoxycholic acid, chenodeoxycholic acid, lithocholic acid, ursocholic acid, ursodeoxycholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and mixtures thereof.

36. The composition of claim 34 wherein said hydrophobic agent is a sterol selected from the group consisting of cholestanol, coprostanol, cholesterol, epicholesterol, ergosterol, ergocalciferol, and mixtures thereof.

37. The composition of claim 34 wherein said hydrophobic agent is a saturated or unsaturated fatty acid comprising about 4 to 20 carbon atoms.

38. The composition of claim 37 wherein said saturated or unsaturated fatty acid is a member selected from the group consisting of butyric acid, valeric acid, caproic acid, caprylic acid, capric acid, lauric acid, myristic acid, palmitic acid, stearic acid, oleic acid, linoleic acid, linolenic acid, eleostearic acid, and mixtures thereof.

39. The composition of claim 25 further comprising a pharmaceutically acceptable carrier admixed with the compound.

40. The composition of claim 25 wherein A, B, or both are from ADP-ribosyltransferases.

41. The composition of claim 25 wherein T comprises a myristylation signal sequence.

42. A composition comprising a compound represented by the formula $(T_m\text{-}A\text{-}X\text{-}B)\text{-}H_n$ or $(A\text{-}X\text{-}B\text{-}T_m)\text{-}H_n$, wherein A is a protein synthesis inactivating toxin that is inactive until X is digested; X is a peptide susceptible to digestion by a viral protease; B is a lectin or a segment thereof, T is a targeting moiety, H is a hydrophobic agent, m is 0 or an integer of at least 1, and n is 1.

43. A composition comprising a compound represented by the formula $(T_m\text{-}A\text{-}X\text{-}B)\text{-}H_n$ or $(A\text{-}X\text{-}B\text{-}T_m)\text{-}H_n$, wherein A is a protein synthesis inactivating toxin that is inactive until X is digested; X is a peptide susceptible to digestion by a viral protease; B is a lectin or a segment thereof, T is a targeting moiety, H is a hydrophobic agent, m is 0 or 1, and n is 1.

* * * * *